(12) United States Patent
Moriya et al.

(10) Patent No.: US 7,949,166 B2
(45) Date of Patent: May 24, 2011

(54) DIAGNOSIS SUPPORT SYSTEM

(75) Inventors: Yoshiyuki Moriya, Minato-ku (JP); Caihua Wang, Minato-ku (JP)

(73) Assignee: Fujifilm Corporation, Tokyo (JP)

( * ) Notice: Subject to any disclaimer, the term of this patent is extended or adjusted under 35 U.S.C. 154(b) by 241 days.

(21) Appl. No.: 12/297,669

(22) PCT Filed: Apr. 12, 2007

(86) PCT No.: PCT/JP2007/058080
§ 371 (c)(1),
(2), (4) Date: Oct. 20, 2008

(87) PCT Pub. No.: WO2007/119788
PCT Pub. Date: Oct. 25, 2007

(65) Prior Publication Data
US 2009/0080734 A1 Mar. 26, 2009

(30) Foreign Application Priority Data
Apr. 19, 2006 (JP) .................... 2006-115574

(51) Int. Cl.
*G06K 9/00* (2006.01)
*A61B 5/00* (2006.01)
*A61B 5/05* (2006.01)

(52) U.S. Cl. .......................... 382/128; 600/300; 600/427

(58) Field of Classification Search .................. 382/128, 382/129, 130, 131, 132, 133, 134, 190; 600/407, 600/410, 443, 300, 425, 427; 128/916, 920, 128/922; 378/4, 21, 901; 702/183
See application file for complete search history.

(56) References Cited

U.S. PATENT DOCUMENTS

| | | | | |
|---|---|---|---|---|
| 6,849,048 B2 * | 2/2005 | Omiya | .......................... | 600/443 |
| 6,925,199 B2 * | 8/2005 | Murao | .......................... | 382/131 |
| 7,616,793 B2 * | 11/2009 | Marshall et al. | .............. | 382/128 |
| 2003/0048265 A1 | 3/2003 | Bito et al. | | |
| 2006/0025671 A1 | 2/2006 | Kusunoki | | |

FOREIGN PATENT DOCUMENTS

| | | |
|---|---|---|
| JP | 7-56947 A | 3/1995 |
| JP | 2005-65728 A | 3/2000 |
| JP | 2002-230518 A | 8/2002 |
| JP | 2003-85194 A | 3/2003 |
| JP | 2004-133728 A | 4/2004 |
| JP | 2006-34585 A | 2/2006 |

* cited by examiner

*Primary Examiner* — Abolfazl Tabatabai
(74) *Attorney, Agent, or Firm* — Sughrue Mion, PLLC

(57) ABSTRACT

A region of interest is set by region of interest setting means in each of medical images obtained in chronological order. Similar case search means searches for a case information set including a case image having a region of similar pictorial characteristics to each of the regions of interest. When the corresponding case information set has been extracted through the search, case information display means displays test result information sets including not only the case images of similar pictorial characteristics but also all case images, test purposes, findings, and the like in the case information sets in chronological order of tests.

6 Claims, 16 Drawing Sheets

10 —
UID : XXXX
DATE OF TEST, TIME OF TEST : 2006/03/31
MODALITY : PLAIN X-RAY IMAGING APPARATUS
NAME OF PATIENT : MARUMI MARUKAWA
PATIENT NUMBER : 2501
AGE : 37
GENDER : FEMALE
EXAMINED BODY PART : CHEST
CONTRAST AGENT/DYE, RADIATION TYPE :
TEST NUMBER : S0008
SERIES NUMBER, ACQUISITION NUMBER :
IMAGE NUMBER : IM6684

FIG.3

TEST NUMBER : S0008
DATE OF TEST, TIME OF TEST : 2006/03/31
MODALITY : PLAIN X-RAY IMAGING APPARATUS
NAME OF PATIENT : MARUMI MARUKAWA
PATIENT NUMBER : 2501
AGE : 37
GENDER : FEMALE
EXAMINED BODY PART : CHEST
CONTRAST AGENT/DYE, RADIATION TYPE :
SERIES NUMBER, ACQUISITION NUMBER :
IMAGE NUMBER : IM6684

PURPOSE OF TEST
      FOLLOW-UP
      EXAMINATION

FINDING
     RIGHT LUNG  TUMOR SHADOW
      SIZE 5mm

LUNG CANCER SUSPECTED

DEGREE OF CERTAINTY 70%

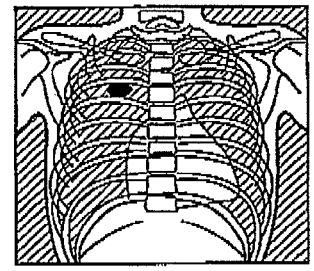

PATIENT INFORMATION —12
  NAME OF PATIENT : MARUMI MARUKAWA
  PATIENT NUMBER : 2501
  AGE : 37
  GENDER : FEMALE
  PREVIOUS DISEASES :
CASE NUMBER : 10521
HISTORY OF TESTS
  TEST NUMBER : S0008
    DATE OF TEST, TIME OF TEST : 2005/04/10
    MODALITY : PLAIN X-RAY IMAGING APPARATUS
    EXAMINED BODY PART : CHEST
    CONTRAST AGENT/DYE, RADIATION TYPE :
    IMAGE NUMBER : IM6684
    FINDING : RIGHT LUNG   TUMOR SHADOW
  TEST NUMBER : S0035
    DATE OF TEST, TIME OF TEST : 2005/12/20
    MODALITY : PLAIN X-RAY IMAGING APPARATUS
    EXAMINED BODY PART : CHEST
    CONTRAST AGENT/DYE, RADIATION TYPE :
    FINDING : RIGHT LUNG   TUMOR SHADOW

HISTORY OF TREATMENTS

FIG.9A
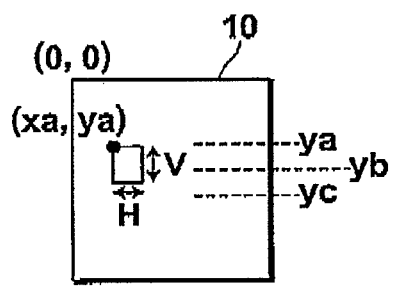
FIG.9B
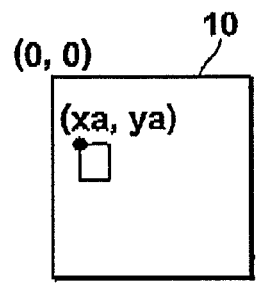
FIG.9C
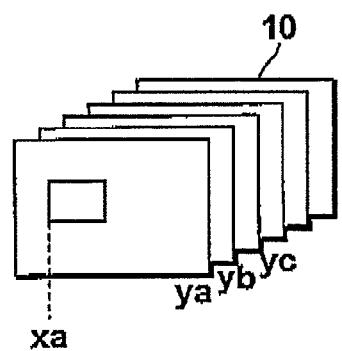
FIG.10
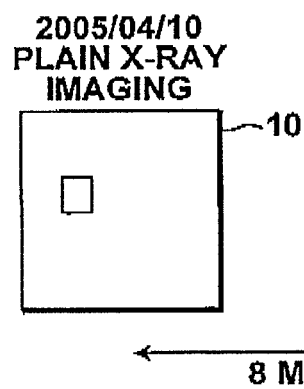
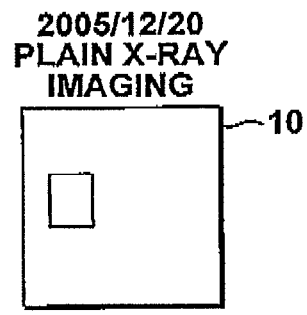
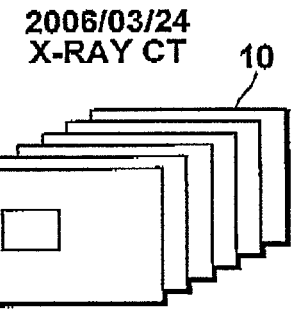

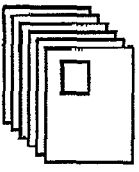
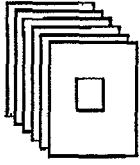
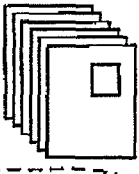
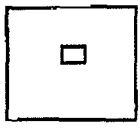
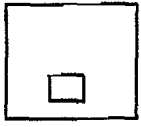
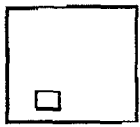
FIG. 14

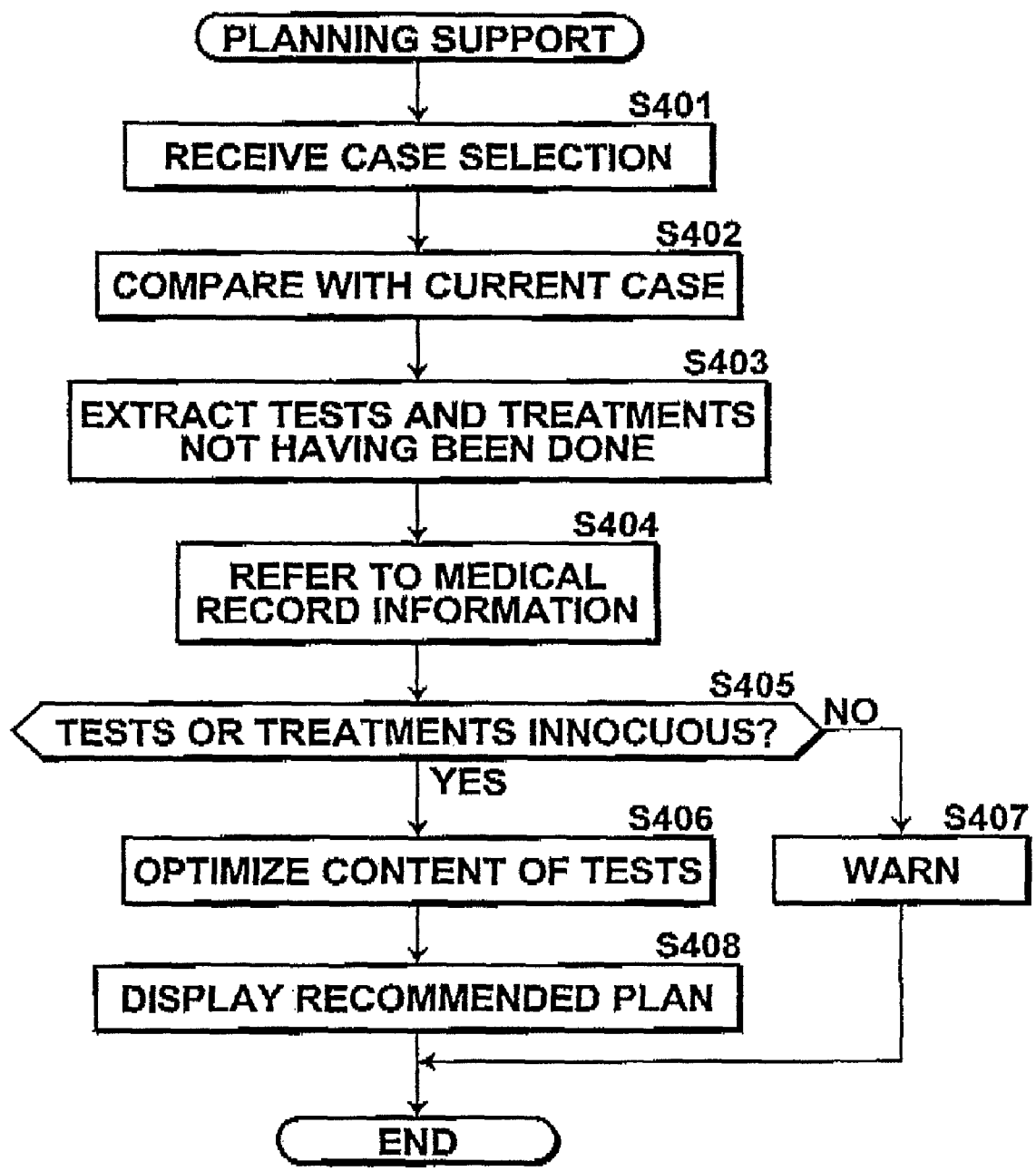

DIAGNOSIS SUPPORT SYSTEM

TECHNICAL FIELD

The present invention relates to a system that can be used for medical imaging diagnosis as well as treatment planning and provides information of similar cases by searching case information collected in past diagnoses and registered with a database.

BACKGROUND ART

In the field of medicine, diagnoses are carried out on presence or absence of diseases and the type or status thereof while medical images generated by imaging of subjects are displayed on monitors and abnormal shadows therein are observed (hereinafter referred to as image interpretation). In addition, functions are provided to display information of cases whose tests have generated images of similar characteristics to images to be interpreted, as a function to support such diagnoses at the time of image interpretation. For example, Japanese Unexamined Patent Publication Nos. 2005-065728 and 2002-230518 describe apparatuses and methods for displaying a reference image having a high degree of similarity and information such as a finding related to the reference image, according to the steps of extracting a lesion location from an image to be diagnosed (hereinafter referred to as an interpretation target image), calculating characteristic quantities representing pictorial characteristics in the extracted lesion location, and finding a degree of similarity between each of reference images stored in a database and the interpretation target image through comparison of the characteristic quantities therebetween.

The conventional apparatuses described above are useful when diagnosis is carried out on a test result (that is, an image) obtained at one time, and have achieved reasonable results. However, in actual diagnosis, accurate diagnosis may not be carried out on a test result obtained only at one time, even if information on an image having a high degree of similarity is used as a reference. In such a case, the same test is generally carried out repeatedly at predetermined intervals, for example, so that diagnosis can be carried out by observation of progression.

As reference information for diagnosing based on a result of progression observation, information on cases representing similar progression of a disease is useful. Information on cases of similar progression is not only usable for diagnosis but also helpful for planning future tests or treatments. However, the conventional apparatuses can search for only information of cases including images similar to an image obtained at one time, as has been described above. Therefore, provision of a system enabling easy extraction of information on cases of similar progression has been desired.

An object of the present invention is therefore to provide a diagnosis support system enabling search and extraction of information on cases showing similar progression.

DISCLOSURE OF THE INVENTION

A diagnosis support system of the present invention is a system that supports diagnosis based on interpretation of a given medical image by searching case information sets registered with a database for case information sets including case images of similar pictorial characteristics to the given medical image and by displaying the case information sets including the case images, and the system comprises region of interest setting means, similar case search means, and case information display means described below.

The region of interest setting means sets a region of interest in each of medical images obtained in chronological order, by displaying the medical images on a monitor screen and by receiving a region specifying operation on at least one of the medical images. The medical images obtained in chronological order refer to medical images obtained in medical tests carried out on the same body part of the same patient on different days or at different times. The types of modalities used in the tests are not necessarily the same as long as the same subject is examined.

The region of interest draws attention at the time of image interpretation, and characteristics thereof greatly affect diagnosis. The region of interest is generally referred to as ROI (Region Of Interest). The region of interest is not necessarily a portion of a medical image, and may be an entire medical image. For example, in the case of chest image interpretation, the whole lungs can be set as the region of interest if the lungs exhibit swelling.

The region of interest is generally but not necessarily the region specified by the region specifying operation. For example, lesion outline extraction processing through image analysis may be carried out in the specified region so that a region in the extracted outline can be set as the region of interest. The region specifying operation is not necessarily carried out on all the medical images. For example, the diagnosis support system may have corresponding region estimating means for estimating in a second one of the medical images a region representing a target that is the same as a target represented by a region specified in a first one of the medical images, according to coordinate information identifying the region specified in the first medical image. The region of interest setting means in this case receives specification of the region of interest by the region specifying operation only in one of the medical images, and causes the corresponding region estimating means to estimate the region of interest in each of the remaining images by supplying the coordinate information identifying the specified region thereto. In this manner, the region of interest can be set in each of the medical images.

The similar case search means extracts through search of the database a case information set including case images each having a region representing pictorial characteristics that are similar to pictorial characteristics of a corresponding one of the regions of interest having been set by the region of interest setting means. For example, in the case where the region of interest setting means has set the regions of interest in first, second, and third medical images, the similar case search means carries out the search in order to extract three case images comprising a first case image having a region representing pictorial characteristics that are similar to pictorial characteristics of the region of interest in the first medical image, a second case image having a region representing pictorial characteristics that are similar to pictorial characteristics of the region of interest in the second medical image, and a third case image having a region representing pictorial characteristics that are similar to pictorial characteristics of the region of interest in the third medical image.

Various procedures can be listed as the procedures of the search carried out by the similar case search means. For example, the similar case search means may carry out the procedures of searching for case images each having a region representing pictorial characteristics that are similar to the pictorial characteristics of a corresponding one of the regions of interest having been set by the region of interest setting means, identifying a group of case images of one and the same patient each having the region representing the pictorial characteristics that are similar to the pictorial characteristics of the corresponding region of interest having been set by the region of interest setting means among the case images having been detected through the search for the case images, and supplying a case information set including the case images belonging to the identified group to the case information display means as the case information set having been extracted through the search of the database.

Alternatively, the similar case search means may carry out the procedures of searching for case images each having a region representing pictorial characteristics that are similar to pictorial characteristics of the region of interest in one of the medical images having been set by the region of interest setting means, further searching for case images respectively having regions representing pictorial characteristics that are similar to pictorial characteristics of the regions of interest in the medical images excluding the one medical image by setting case information sets including the case images extracted through the search for the case images as a search range, and supplying a case information set from which the case images respectively having the regions representing the pictorial characteristics that are similar to the pictorial characteristics of the regions of interest in the corresponding medical images other than the one medical image have been extracted to the case information display means as the case information set having been extracted through the search of the database.

The case information display means displays all the case images belonging to the case information set extracted by the similar case search means on the monitor screen in chronological order. In a system according to an embodiment of the present invention, the case information display means collectively displays only identifiers of the extracted case information sets and receives an operation of selection from the identifiers. The case information display means displays all the case images belonging to the case information set represented by the identifier selected by the operation, in chronological order of acquisition of the case images. At this time, if the case images respectively having the regions representing the pictorial characteristics that are similar to the pictorial characteristics of the regions of interest are displayed distinctly from the other case images included in the case information set to which the case images belong, the images used for similarity judgment can be distinguished easily.

In addition, if the diagnosis support system described above further comprises time interval setting means for setting an acquisition time interval between the medical images so that the similar case search means can search the database for a case information set that includes case images obtained at a time interval equal to the time interval having been set by the time interval setting means and respectively have the regions representing the pictorial characteristics that are similar to the pictorial characteristics of the regions of interest in the corresponding medical images having been set by the region of interest setting means, the case whose manner of lesion change (for example, a manner of growth or change in color) and a pace of disease progression are similar can also be extracted through the search. In this manner, cases of higher similarity can be used as reference information for diagnosis.

Since the diagnosis support system of the present invention has the region of interest setting means for setting the region of interest in each of the medical images obtained in chronological order and the similar case search means for collectively carrying out similarity search for all the regions of interest having been set by the region of interest setting means, a temporal change in the pictorial characteristics can be used as a query for the similar case search. Therefore, information of cases representing similar disease progression can be obtained and provided through the search. Especially, in an embodiment where the time interval at which the images have been obtained is also set as a query for the similar case search, a case showing similarity not only in a change in a disease but also in a progression speed can be searched for. Therefore, cases with extremely similar disease progression can be extracted. Information on the cases of similar progression is useful not only as a reference for diagnosis but also for planning of future tests and treatments.

BRIEF DESCRIPTION OF THE DRAWINGS

FIG. 3 shows an example of an image interpretation report;

FIG. 4 shows an example of a medical record information set;

FIGS. 9A to 9C schematically show a method of estimating an ROI;

FIG. 10 shows an example of ROI having been set by the region of interest setting means;

FIG. 14 schematically shows second similar case search procedures;

FIG. 19 is a flow chart showing treatment planning support processing.

BEST MODE FOR CARRYING OUT THE INVENTION

Figures 1, 2:
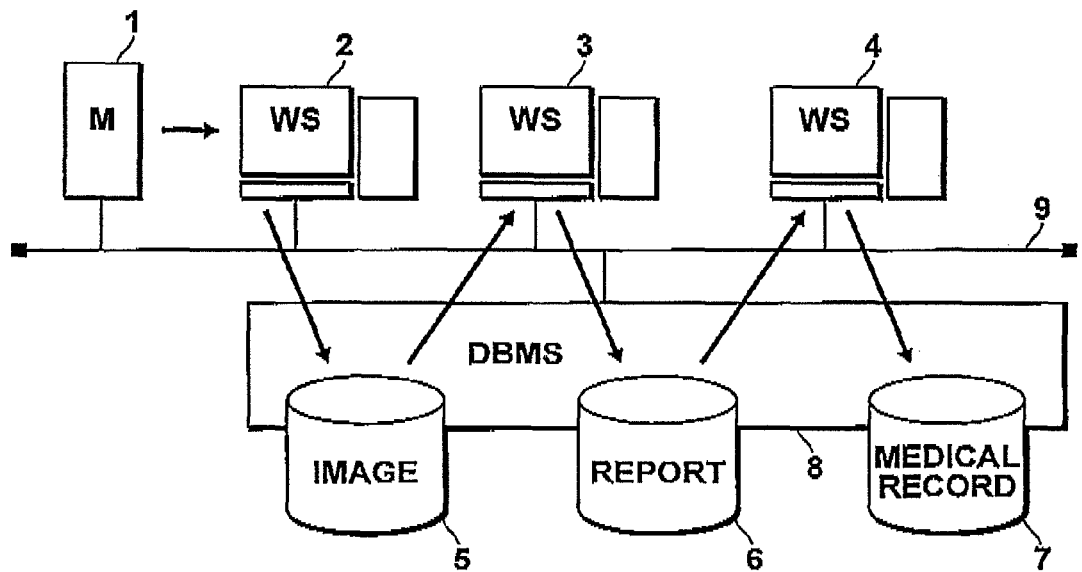
FIG. 1 shows the configuration of a diagnosis support system having a similar case search function.
FIG. 2 shows an example of a medical image information set.

FIG. 1 schematically shows the configuration of a medical information processing system to which a diagnosis support system of an embodiment of the present invention has been introduced. As shown in FIG. 1, the system comprises imaging apparatuses (hereinafter referred to as modalities) (M) 1, clinical technologist workstations (WS: WorkStation) 2, radiologist workstations (WS) 3, physician workstations (WS) 4, an image information database 5, an image interpretation report database 6, a medical record information database 7, and a database management server (DBMS: DataBase Management Server) 8 for managing the three types of databases, all of which are connected via a network 9 to be communicable to each other. FIG. 1 shows the configuration including only one apparatus of each of the types, for the sake of simpler description. However, the network 9 connects a plurality of modalities of various types as the modalities 1, and the numbers of the clinical technologist workstations 2, the radiologist workstations 3, and the physician workstations 4 respectively correspond to the numbers of clinical technologists, radiologists, and physicians.

In this embodiment, the network 9 is a local area network connecting the various apparatuses in a hospital. However, in the case where the physician workstations 4 are also installed in another hospital or clinic, the network 9 may connect local area networks of the respective hospitals via the Internet or a dedicated line. In either case, it is preferable for the network 9 to be an optical network or the like that can realize high-speed image information transfer.

Each of the modalities 1 generates image data by imaging a subject, and adds accompanying information defined by the DICOM standard to the image data to output the data added with the accompanying information as an image information set. In this specification, the combination of image data representing a subject and accompanying information added thereto is referred to as an "image information set". In other words, an image information set includes text information related to an image. The modalities 1 may be modalities that carry out imaging of subjects as well as image data generation, or modalities each comprising an imaging apparatus for recording an image on a recording sheet and a reading apparatus that is separated from the imaging apparatus and reads the image from the recording sheet to generate image data. More specifically, the modalities may be apparatuses performing plain X-ray imaging, CT (Computed Tomography), MR (Magnetic Resonance) imaging, PET (Positron Emission Tomography), and ultrasonography, for example.

Each of the clinical technologist workstations 2 comprises a general-purpose processor (computer), one or two high-definition displays, and input devices such as a mouse and a keyboard. Software for supporting the work of clinical technologists has been installed in the respective processors. According to functions of the software, the clinical technologist workstations 2 receive the image information sets according to the DICOM standard from the modalities 1, and prompt the clinical technologists to confirm the content of the image data and the accompanying information included in the received image information sets by display of the content on screens. The workstations 2 then transfer the image information sets having been confirmed by the clinical technologists to the DBMS 8 via the network 9, and request registration of the image information sets with the image information database 5.

The DBMS 8 is a comparatively high-performance general-purpose computer in which a software program for providing functions of the DBMS has been installed. The DBMS 8 stores the data whose registration has been requested in a large-capacity storage connected to the DBMS 8, and extracts and provides data that match a search condition when viewing is requested regarding the data having been registered. However, the data may be stored in a NAS (Network Attached Storage) or a SAN (Storage Area Network) connected to the network 9.

Upon reception of registration request regarding the image information sets, the DBMS 8 registers the image information sets with the image information database 5 after formatting the image information sets into a format for the database. FIG. 2 shows an example of the image information sets registered with the image information database 5.

An image information set 10 is managed as XML or SGML data, for example, and comprises image data representing an image of a subject and accompanying information including at least patient number for identifying the subject, test number for identifying a test, and image number for identifying the image, as shown in FIG. 2. In addition, the accompanying information includes information such as unique ID (UID) that is assigned to each of the image information sets, date of test on which the image information set was generated, time of test, type of modality used in the test for obtaining the image information set, patient information including name, age, gender, and the like of the patient, examined body part (imaged body part), imaging conditions (use or non-use of contrast agent/dye used in imaging, type of radiation, dose of radiation, and the like), and series number or acquisition number in the case where a plurality of images were obtained in one test.

When the DBMS 8 receives a viewing request from any one of the radiologist workstations 3 via the network 9, the DBMS 8 searches the image information sets registered with the image information database 5, and sends an extracted portion of the image information sets to the radiologist workstation 3 having sent the request thereto.

Each of the radiologist workstations 3 is an apparatus used by the radiologists for image interpretation, and comprises a processor, one or two high-definition displays, and input devices such as a mouse and a keyboard. The processor has functions to support diagnosis by radiologists, such as a function to highlight a part that seems to be a lesion in an image by automatically detecting the part and a function to support generation of an image interpretation report. When an image interpretation screen of any one of the workstations 3 is operated for requesting viewing of an interpretation target image and information to be used for diagnosis, the workstation 3 sends a viewing request to the DBMS 8 and obtains the image information set that is necessary for image interpretation or diagnosis. The radiologist workstation 3 displays the image information set on a monitor screen, and carries out the automatic lesion detection processing and the like according to a request made by any one of the radiologists.

In addition, the radiologist workstation 3 displays a report generation screen on the monitor for supporting generation of an image interpretation report. When the radiologist inputs text representing the content of diagnosis (such as a finding) based on image interpretation, the radiologist workstation 3 generates an image interpretation report that records the inputted information and the image having been interpreted (hereinafter referred to as the interpretation target image). In the case where more than one interpretation target images exist, one of the images that influenced the diagnosis most (hereinafter referred to as the representative image) is recorded in the report. The radiologist workstation 3 transfers the generated image interpretation report to the DBMS 8 via the network 9, and requests registration of the image interpretation report with the image interpretation report database 6. Upon reception of the request, the DBMS 8 registers the image interpretation report with the image interpretation report database 6 after formatting the image interpretation report according to a format for the database. FIG. 3 shows an example of the image interpretation report registered with the image interpretation report database 6.

An image interpretation report 11 is managed as XML or SGML data, for example, and comprises image data representing the interpretation target image or the representative image, information such as the test number, the patient number, and the image number obtained by referring to the accompanying information at the time of interpretation of the image, a finding, information representing a degree of certainty, and the like, as shown in FIG. 3. The image data may be an exact copy of the image data included in the corresponding image information set 10, or reduced image data (thinned image data) having a fewer number of pixels than the image data included in the image information set 10. Alternatively, the image data may be link information to a storage location (such as a folder) and file name of the image data in the image information database 5. It is preferable for the image interpretation report 11 to record, in addition to the image data, coordinate information representing a region of interest (hereinafter also referred to as ROI) having been set in the image data at the time of image interpretation. The coordinate information representing the ROI may be recorded not only in the image interpretation report 11 but also in the accompanying information of the corresponding image information set 10.

Upon reception of a viewing request from any one of the physician workstations 4 via the network 9, the DBMS 8 searches the image interpretation reports registered with the image interpretation report database 6, and sends an extracted portion of the image interpretation reports to the physician workstation 4 having sent the request.

Each of the physician workstations 4 is an apparatus used by any one of the physicians to refer to the image interpretation report and the interpretation target image, and comprises a processor, one or two high-definition displays, and input devices such as a mouse and a keyboard. The processor has a function to generate a medical record information set for recording history of examinations, tests, and treatments (such as medication) as electronic data, and an test ordering function to generate and send test order information to an order system (not shown) of a radiology department.

The physician workstation 4 newly generates the medical record information set that records the patient information, purpose of examination, and the like, at the first time of examination of the patient. The workstation 4 sends the medical record information set to the DBMS 8 via the network 9, and requests registration of the medical record information set with the medical record information database 7. When the DBMS 8 receives the registration request regarding the medical record information set, the DBMS 8 registers the medical record information set with the medical record information database 7 after formatting the medical record information set according to a format for the database.

When a test is ordered during examination by the test ordering function described above, the physician workstation 4 adds the test number, the date of test, and the like notified from the system in the radiology department to the medical record information set. Furthermore, in the case where one of the radiologists has generated the image interpretation report 11 after completion of the test and the physician refers to the image interpretation report 11, the physician workstation 4 adds a portion of the information in the image interpretation report (such as a finding by the radiologist) to the medical record information set.

Meanwhile, information inputted by the physician himself/herself is also added to the medical record information set from time to time. For example, in the case where a test without imaging, such as a blood test, is carried out, information on finding inputted by the physician referring to a result of the test is added to the medical record information set. In addition, treatment records such as medication is inputted by the physician and added to the medical record information set. The physician workstation 4 transfers the updated medical record information set or difference information representing only the updated portion to the DBMS 8, and requests update of the medical record information set.

Upon reception of the medical record update request, the DBMS 8 calls up the medical record information set in a memory by searching the medical record information database 7, and updates the content thereof in the memory. Thereafter, the DBMS 8 writes the updated medical record information set in the storage. In this manner, the content of the medical record information database 7 is updated.

FIG. 4 shows an example of the medical record information sets registered with the medical record information database 7. A medical record information set 12 is managed as XML or SGML data, for example, and records the patient information registered at the time of first examination, history of examinations, test history, and treatment history including medication of the patient as has been described above, in addition to information necessary for examinations and treatments such as previous and chronic diseases and allergies. In this embodiment, the medical record information set 12 records at least the patient number and the test number identifying a test carried out in the past. The medical record information set 12 shown in FIG. 4 has no image data. However, reduced image data or link information to the corresponding image information set may be recorded as an item of the test history, as in the image interpretation report 11.

As has been described above, the image information sets registered with the image information database 5 and the image interpretation reports registered with the image interpretation report database 6 are related to each other at the time of imaging diagnosis using the radiologist workstations 3. Furthermore, the image interpretation reports registered with the image interpretation report database 6 and the medical record information sets registered with the medical record information database 7 are related to each other at the time of generation and update of the medical record information sets with use of the physician workstations 4. In this manner, the three types of information comprising the image information sets, the image interpretation reports, and the medical record information sets are related to each other.

Figure 5:
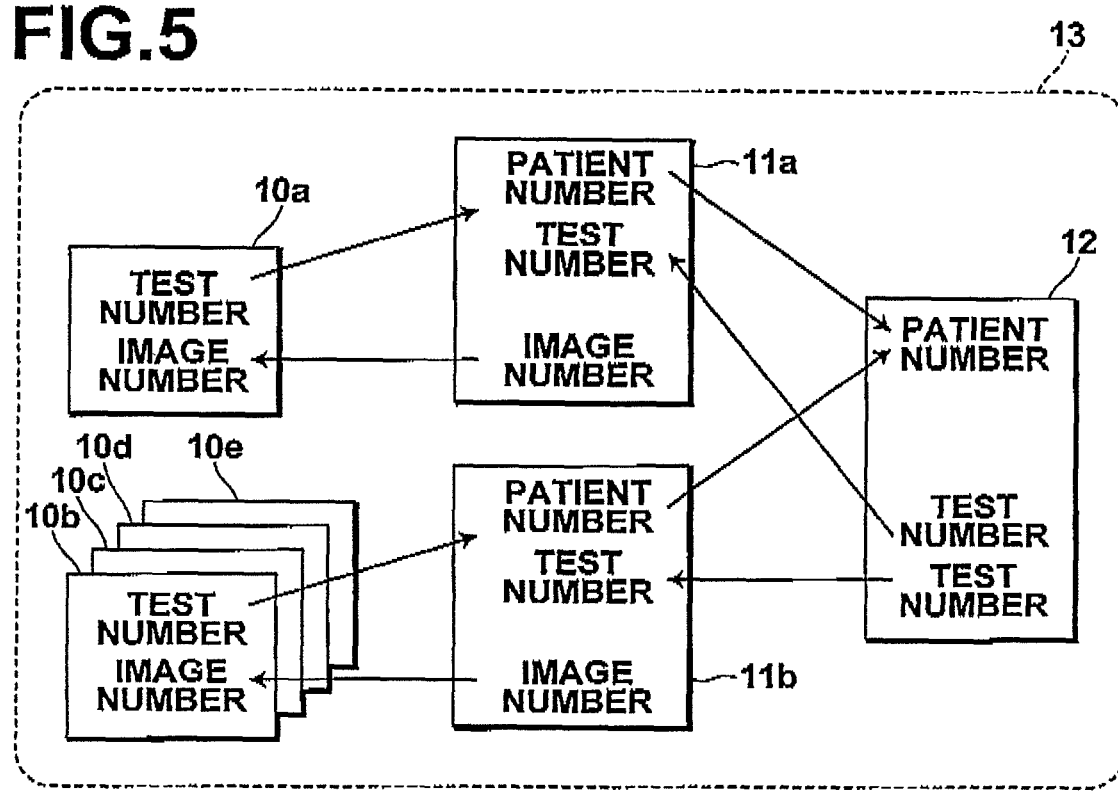
FIG. 5 shows relationships between the medical image information sets, the image interpretation reports, and the medical record information set.

FIG. 5 shows the data used to relate the three types of information and how the information is related. In this embodiment, as shown in FIG. 5, an image information set 10a related to plain X-ray imaging, image information sets 10b to 10e comprising series images obtained in a CT scan or the like, and image interpretation reports 11a and 11b respectively include information on the test number assigned to each of the tests. Therefore, in the case where the image interpretation report corresponding to a given one of the image information sets is needed, the image interpretation report database 6 is searched by using the test number as a search key, and the report can be obtained.

Meanwhile, each of the image interpretation reports 11a and 11b has the image number of the corresponding interpretation target image. Therefore, in the case where the image information set referred to at the time of generation of a given one of the image interpretation reports needs to be obtained according to the report, the image information database 5 is searched by using the image number as a search key. In this manner, the image information set can be obtained. Alternatively, in the case where the image interpretation report has the link information to the storage location of the image information set, the image information set referred to at the time of generation of the image interpretation report can be obtained immediately by following the link information. In the case where the image interpretation report has the image numbers of a plurality of images or a plurality of items of the link information, the corresponding image information sets can be obtained in the same manner.

In the case where all images belonging to a series need to be obtained from one of the image interpretation reports such as the image interpretation report 11b shown in FIG. 5 in which only the image number regarding the representative image has been recorded, all the image information sets of the series can be obtained by searching the image information database 5 with the test number as a search key.

In addition, as shown in FIG. 5, the image interpretation reports 11a and 11b and the medical record information set 12 respectively have the information on the patient number and the test number. Therefore, in the case where the corresponding medical record information set needs to be obtained based on a given one of the image interpretation reports, the medical record information set can be obtained by searching the medical record information database 7 with the patient number as a search key. In the case where the information on one of the tests recorded in the medical record information set 12 needs to be obtained from the medical record information set, search of the image interpretation report database 6 followed by search of the image information database 5 is carried out with the test number as a search key. In this manner, the corresponding image information set and the corresponding image interpretation report generated in the test can be obtained.

In other words, in this embodiment, the image information sets 10, the image interpretation reports 11, and the medical record information sets 12 are related to each other although registered separately with the databases for the sake of data management, all case information related to any one of the image information sets 10, any one of the image interpretation reports 11, or any one of the medical record information sets 12 can be obtained and referred to by specifying the one information set. Hereinafter, the combination of the information sets related to each other is referred to as a case information set 13.

Although the case information set can be identified by the image number, the patient number, or the test number as has been described above, identification of the patient at the time of referring to the case is not necessarily preferable in terms of personal information protection. Therefore, in this embodiment, case number is assigned to the case information set 13 separately from the patient number, and a person who accesses the case information set upon necessity can distinguish the case only by the case number without knowing the patient number. The case number is recorded in the corresponding electronic medical record information set 12.

Hereinafter, how the similar case search function is realized 3 will be described further, as one of the diagnosis support functions provided by the radiologist workstations.

Figure 6:
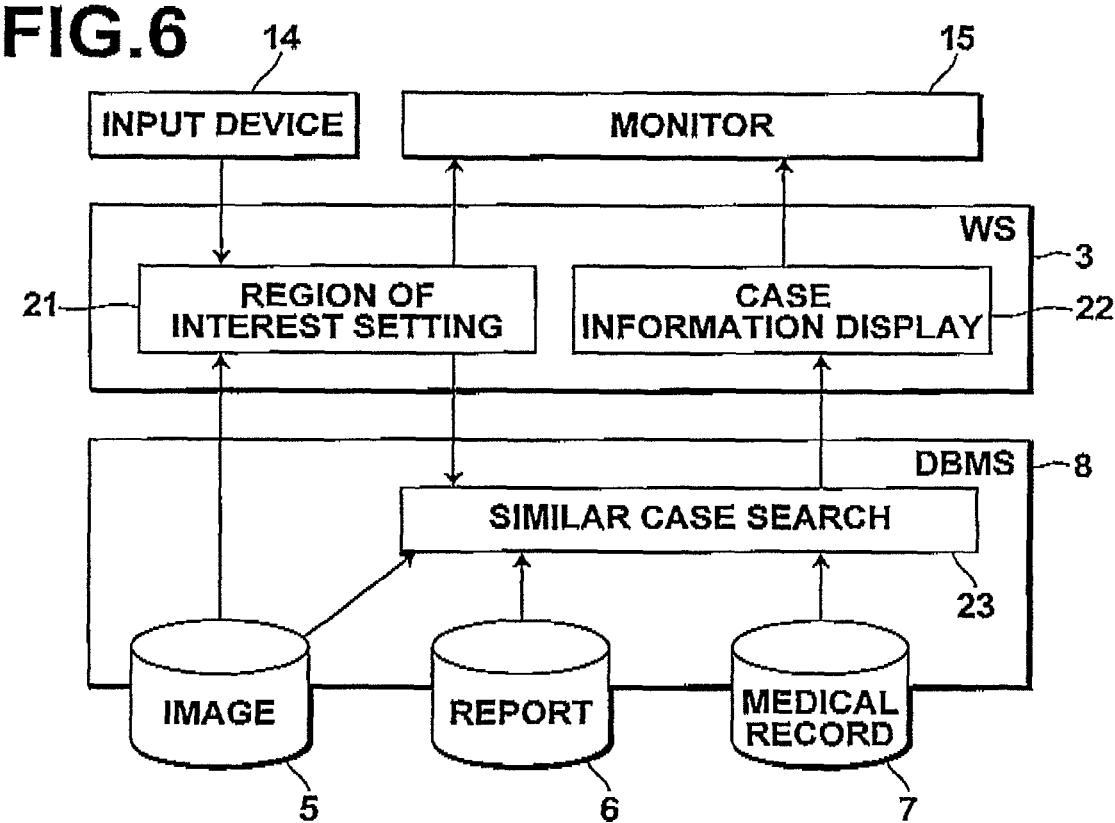
FIG. 6 shows an example of the configuration to realize the similar case search function.

FIG. 6 shows an example of the configuration of each of the radiologist workstations 3 and the DBMS 8 for realizing the similar case search function. As has been described above, the radiologist workstations 3 have the various diagnosis support functions other than the similar case search function, which are neither described nor shown here.

As shown in FIG. 6, in this embodiment, an input device 14 such as a mouse and a monitor 15 are connected to each of the radiologist workstations 3. Each of the radiologist workstations 3 has region of interest setting means 21 for setting a region image used as a query at the time of case search (hereinafter referred to as a query image), and case information display means 22 for controlling display of case information sets extracted through the search. The DBMS 8 has similar case search means 23 for searching for the case information sets based on the query image supplied from the region of interest setting means 21 and for transferring the extracted case information sets to the case information display means 22 of the corresponding radiologist workstation 3.

In this embodiment, the functions of the region of interest setting means 21, the case information display means 22, and the similar case search means 23 are realized by execution of procedures defined in programs of the respective apparatuses by CPUs therein. However, the functions of the region of interest setting means 21, the case information display means 22, and the similar case search means 23 may be realized by hardware such as dedicated processors executing only the procedures carried out by the respective means.

Figure 7:
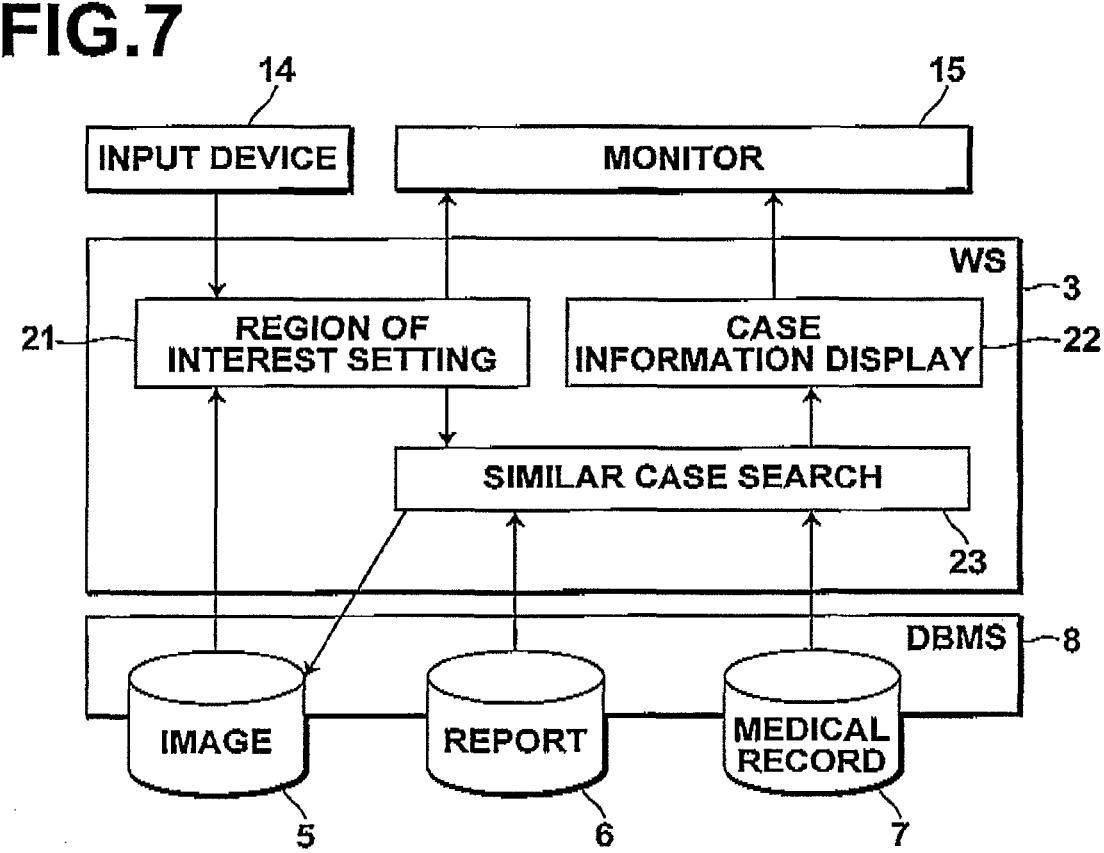
FIG. 7 shows another example of the configuration to realize the similar case search function.

As the configuration to realize the similar case search function, the configuration shown in FIG. 7 can also be used. More specifically, each of the radiologist workstations 3 may have the similar case search means 23. However, in the configuration shown in FIG. 7, whenever the similar case search means 23 accesses the databases, data need to be transferred via the network 9. Therefore, in terms of transfer efficiency of the network and processing efficiency of the whole system, the configuration shown in FIG. 6 is preferable.

Figure 8:
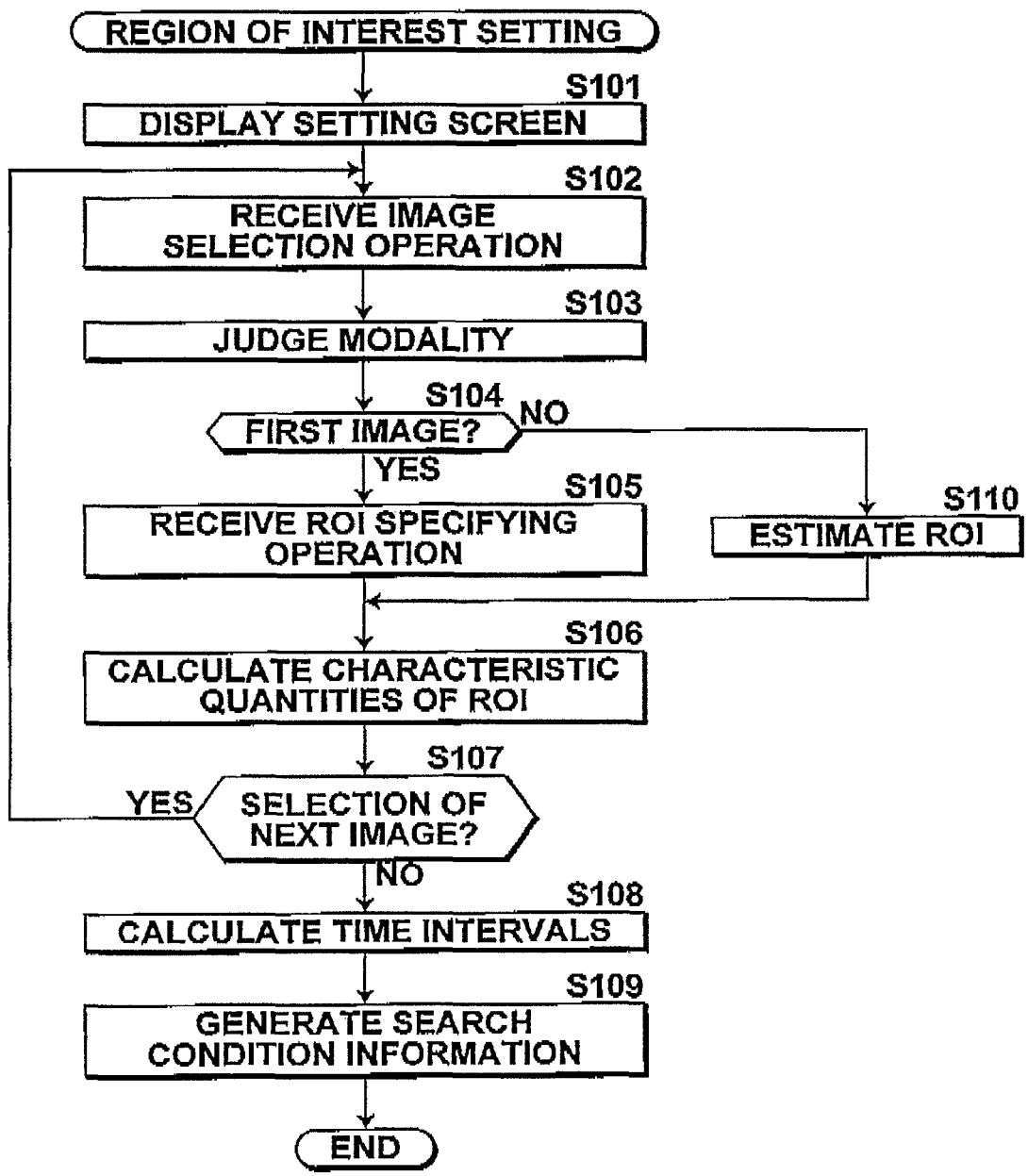
FIG. 8 is a flow chart showing an example of procedures carried out by region of interest setting means.

FIG. 8 is a flow chart showing schematic procedures by the region of interest setting means 21. When any one of the radiologist workstations 3 is operated for requesting similar case display, the region of interest setting means 21 therein displays a search condition setting screen on the monitor 15 (S101). An input box for inputting the image number assigned to each of the images is displayed in the search condition setting screen. Alternatively, a catalog of selectable reduced images is displayed. The region of interest setting means 21 receives information inputted in the input box or a selection operation on the catalog (S102).

Thereafter, the region of interest setting means 21 accesses the image information database 5, and obtains the image information set 10 including the specified image. The region of interest setting means 21 then judges the modality by which the image data of the image information set 10 were generated, by referring to the modality information (shown in FIG. 2) in the accompanying information of the image information set 10 (S103).

If the image selected at Step S102 is a firstly selected image (104), the region of interest setting means 21 outputs the image data of the image information set 10 in a screen of the monitor 15 and receives an ROI specifying operation (S105).

In the case where the image information set 10 has been obtained before the similar case display requesting operation and the ROI has been set in the image data included in the image information set, the region of interest setting means 21 displays in the screen of the monitor 15 the medical image together with a frame representing the ROI having been set. At this time, the ROI may be corrected upon necessity by reception of an ROI resetting operation.

Thereafter, the region of interest setting means 21 calculates a plurality of types of characteristic quantities representing characteristics of a shadow included in the ROI having been set at Step S105 (S106). A size (diameter) of the shadow and a luminance histogram can be listed as the characteristic quantities to be calculated. However, the types of the characteristic quantities that best represent the characteristics of the shadow vary, depending on the type of the shadow (that is, the disease). Therefore, the region of interest setting means 21 judges the type of the shadow (such as lumpy, linear, or cellular) through image analysis of the ROI. The region of interest setting means 21 then selects the characteristic quantities appropriate for identification of the shadow of the type, and calculates the characteristic quantities.

The region of interest setting mean 21 then displays a message inquiring whether another query image is selected and set in the monitor screen (S107). At this time, operation buttons (such as YES and NO buttons) for inputting a response is also displayed in the monitor screen, together with the message. In the case where a subsequent setting operation is carried out, the region of interest setting means 21 returns to Step S102 for reception of subsequent image selection.

In selection of the second or subsequent image selection (S104) in this embodiment, the region of interest setting means 21 carries out ROI estimation processing at Step S110, instead of Step S105. The ROI estimation processing is to estimate an ROI in the second image, based on the ROI set in the first image at Step S105.

FIGS. 9A to 9C show the ROI estimation processing at Step S110. For example, as shown in FIG. 9A, assume that the selected first image is a plain X-ray image and a region having a base point at (xa, ya) and predetermined vertical and horizontal widths V and H has been set as the ROI therein. In this case, if the selected second image is also a plain X-ray image like the first image, the region of interest setting means 21 automatically sets a region having a base point at (xa, ya) and the vertical and horizontal widths V and H in the second image. Alternatively, the region of interest setting means 21 may automatically set as the ROI a region whose horizontal and vertical widths are H and V respectively in the second image after carrying out alignment processing on the second image according to a method described in Japanese Unexamined Patent Publication No. 2002-092589.

In the case where the first image is a plain X-ray image and the second image is series images obtained in a CT scan as shown in FIG. 9C, which section position (ya, yb, or yc) shown in FIG. 9A each of the images in the series has been obtained at can be judged based on the series number or the acquisition number included in the accompanying information of the corresponding image information sets 10. The coordinate system defined in the plain X-ray image is approximately correlated to the coordinate system defined in the CT series images, and an ROI is set automatically in each of the series images. Another technique to correlate regions representing the same target in different images has been described in Japanese Unexamined Patent Publication No. 2004-180932 or the like (although the technique described in Japanese Unexamined Patent Publication No. 2004-180932 does not set an ROI as a query image for similar case search), and detailed description thereof is omitted here.

Since the images obtained chronologically are selected at Step S102, the subject and the ROI is supposed to be the same between the images. However, a size of the ROI may need to be changed in accordance with a temporal change in lesion size. Therefore, in this embodiment, a frame representing the estimated ROI is displayed in superposition of the selected image in the monitor screen in the ROI estimation processing at Step S110. The size of the ROI can be adjusted upon necessity by reception of an enlargement/reduction operation regarding the displayed frame.

The reception of ROI specifying operation at Step S105 may always be carried out regardless of whether the image is the first image or the second or subsequent image (that is, without judgment at Step S104). The ROI estimation processing at Step S110 is to reduce a burden on an operator for ROI setting in the screen, and is not absolutely necessary for the similar case search function.

In the case where an operation for not selecting a subsequent image is carried out at step S107 in FIG. 8, the region of interest setting means 21 calculates an acquisition time interval between the selected images (S108).

In order to calculate the time interval, the information on date and time of test exemplified in FIG. 2 is referred to in the accompanying information in the image information sets of the respective images, and the images set as search conditions are arranged in chronological order based on the test date and time. In this embodiment, the images are sorted in descending chronological order of the test date and time. Thereafter, by calculating the difference in the test date and time between every two neighboring ones of the images, the acquisition time intervals between the images can be found.

The region of interest setting means 21 then generates a search condition information set combining as search conditions the time intervals calculated at Step S108 and the characteristic quantities calculated at Step S106 (S109). However, in the case where the time intervals are set as a part of the search conditions, the time intervals found through the calculation are set after being converted into predetermined time unit. In this embodiment, the time intervals are set by using a half-month as a time unit. For example, if the time interval found by the calculation is 18 days 15 hours and 20 minutes, the time interval is converted into 0.5 month. If the calculated time interval is 35 days 3 hours and 13 minutes, the time interval is converted into 1 month. If the time interval is 72 days 2 hours and 1 minute, the time interval is converted into 2.5 month. In this manner, the time intervals are rounded to the nearest half-month.

The search condition information set generated at Step S109 is transferred to the DBMS 8 as shown by an arrow in FIG. 6, and supplied to the similar case search means 23.

FIG. 10 shows an example of the images and the ROIs set in the region of interest setting processing in order of acquisition of the images, and shows the case where chest CT images obtained on Mar. 24 of 2006, a plain chest X-ray image obtained on Dec. 20 of 2005, and a plain chest X-ray image obtained on Apr. 10 of 2005 have been selected at Step S102 in FIG. 8 and ROIs having rectangular shapes shown therein have been set at Step S105 or S110. In this example, the acquisition time intervals between the images are 3 months and 8 months. The newer the images are, the larger the ROIs have been set, as the suspicious shadow has gradually grown.

Figure 11:
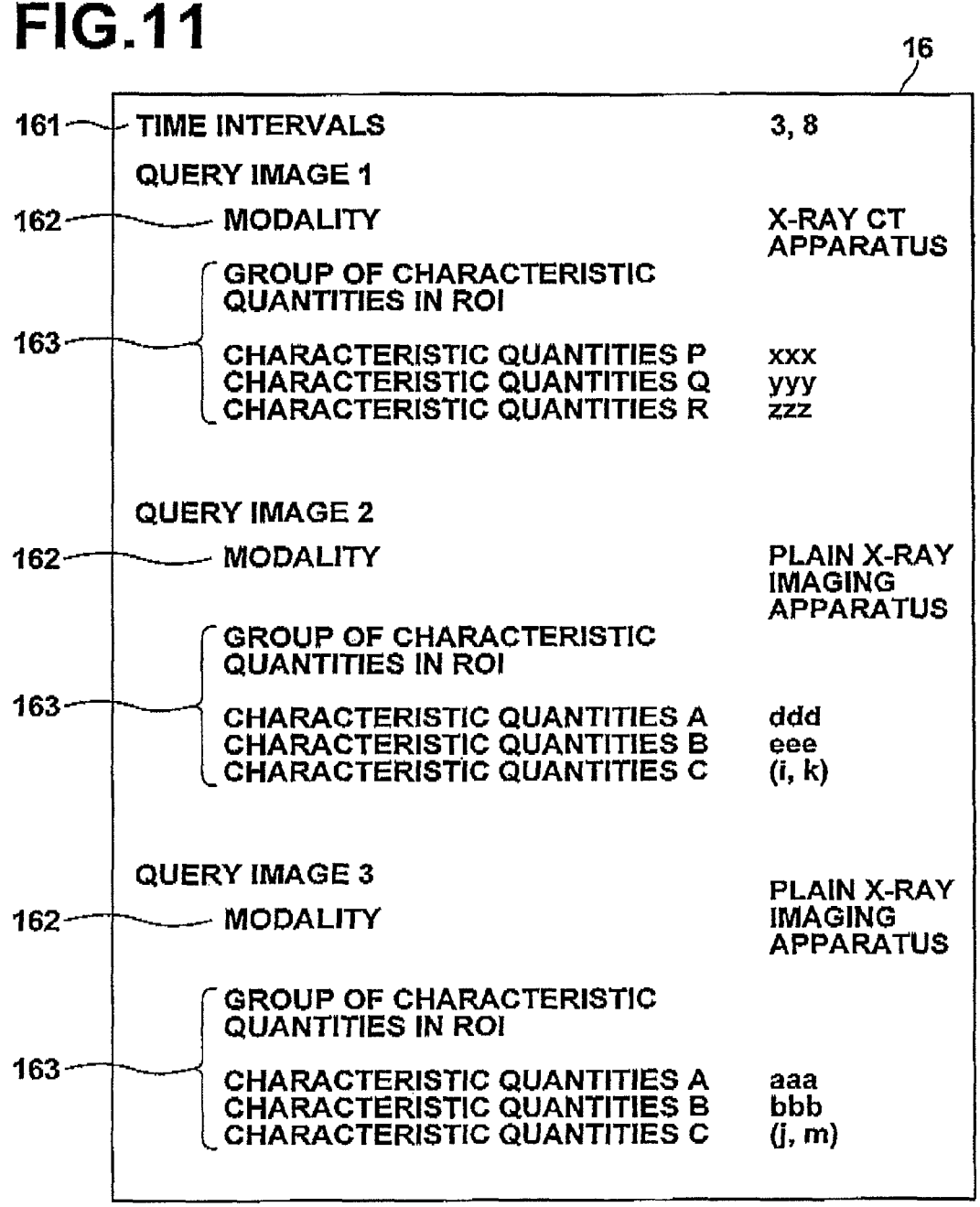
FIG. 11 shows an example of a search condition information set generated by the region of interest setting means.

FIG. 11 shows an example of a search condition information set 16 generated by the region of interest setting means 21 in the case where the images obtained at the three times and the ROIs exemplified in FIG. 10 have been set. In this embodiment, in the case where a plurality of query images have been set, the region of interest setting means 21 generates the search condition information set 16 to include information 161 on the image acquisition time intervals. The image acquisition time interval information 161 is set as values separated by comma, as shown in FIG. 11 for example. In the example shown in FIG. 10, the time intervals are 3 months and 8 months. Therefore, the image acquisition time interval information 161 is set as "3, 8".

The search condition information set 16 also includes information 162 on the modalities that generated the image data and values 163 of the characteristic quantities calculated at Step S106 in FIG. 8. These items of information are arranged in ascending or descending chronological order of the test date. FIG. 11 shows the case of descending order.

In this embodiment, the region of interest setting means 21 calculates the time intervals and supplies the information thereon to the similar case search means 23. However, the similar case search means 23 may calculate the time intervals and set the time intervals as search queries. If the information on the test date and time is available for each of the query images in the search condition information set 16 instead of the time interval information 161, the similar case search means 23 can find the image acquisition time intervals by calculating the difference in the test date and time after reception of the search condition information set 16, and can carry out the search by using the time intervals as the search queries.

Hereinafter, the processing carried out by the similar case search means 23 will be described. In the case where only one combination of the modality information and values of the characteristic quantities exists for the query image included in the search condition information set 16, the similar case search means 23 assigns the values of the characteristic quantities of the query image and values of the characteristic quantities calculated from each of the image information sets registered with the image information database 5 to a predetermined arithmetic expression, to find a degree of similarity in the pictorial characteristics between the regions of interest in the two images. In this manner, the similar case search means 23 extracts the image information sets having a high degree of similarity.

Thereafter, the similar case search means 23 obtains the image interpretation report and the medical record information set related to each of the extracted case images, and other image interpretation reports or image information sets related to the medical record information set, through search of the databases by using the relationships described with reference to FIG. 5. In other words, the similar case search means 23 obtains the case information sets 13 and sends the case information sets to the case information display means 22.

In the case where two or more combinations exist in the information of query images included in the search condition information set 16, the similar case search means 23 obtains the case information sets including images similar to the respective query images.

For example, in the case where the query images obtained at the three times shown in the example in FIG. 10 have been set, the similar case search means 23 obtains the case information sets 13 each having the three types of images comprising a plain X-ray image including an ROI representing a target having similar pictorial characteristics to the image in the ROI (hereinafter referred to as the ROI image) of the plain X-ray image obtained on Apr. 10 of 2005, a plain X-ray image including an ROI representing a target having similar pictorial characteristics to the ROI image of the plain X-ray image obtained on Dec. 20 of 2005, and X-ray CT images including an ROI representing a target having similar pictorial characteristics to the ROI image of the X-ray CT images obtained on Mar. 24 of 2006. In other words, the similar case search means 23 obtains the case information sets 13 regarding cases of similar progression of the disease observed in the images. The case information sets are sent to the case information display means 22.

Hereinafter, two sets of procedures will be described as the procedures of search processing in the case where the number of query images is larger than one. However, other search methods can be adopted, and the similar case search means 23 may carry out the search by using any one of the methods.

Figure 12:
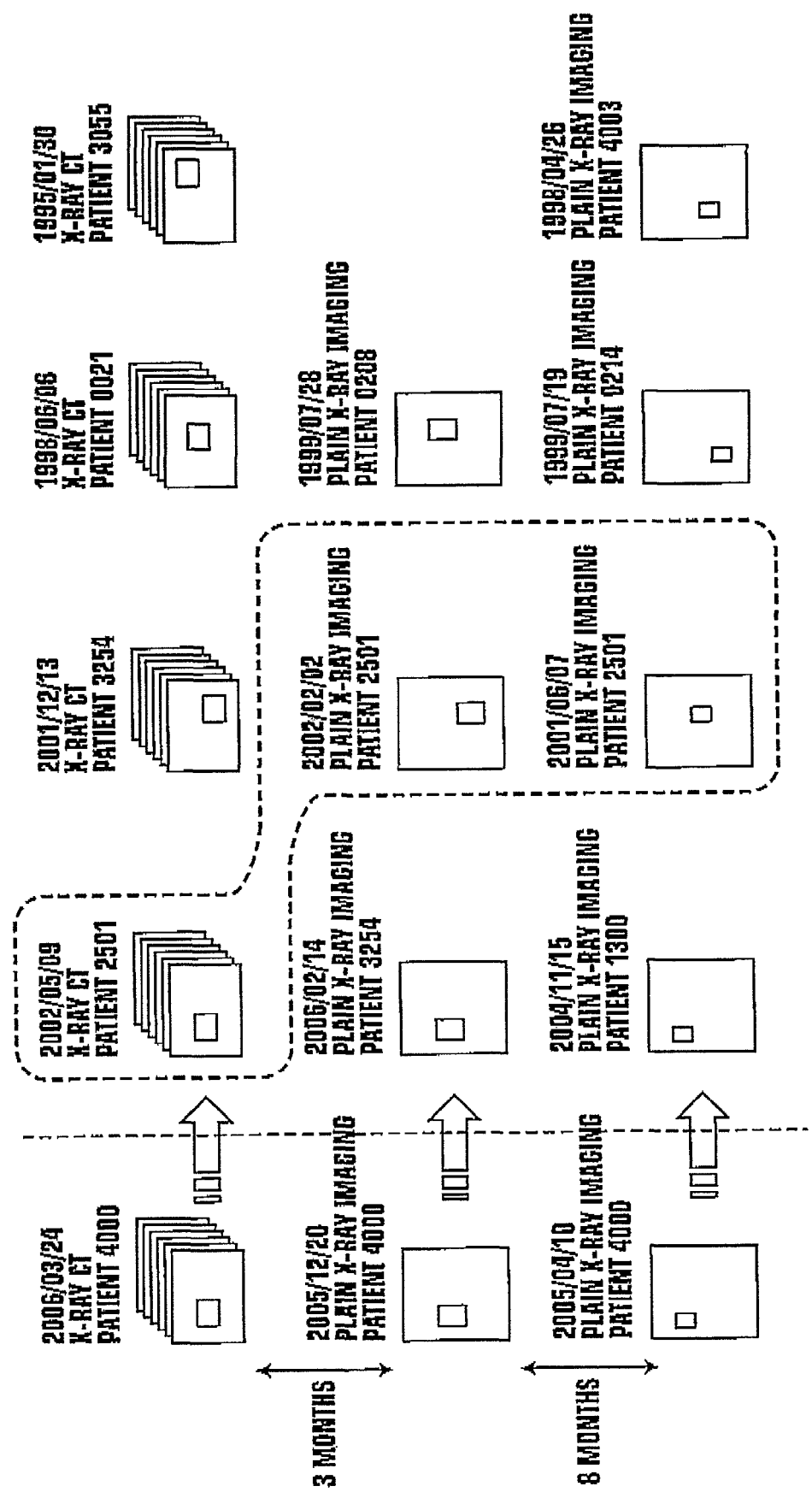
FIG. 12 schematically shows first similar case search procedures.
Figure 13:
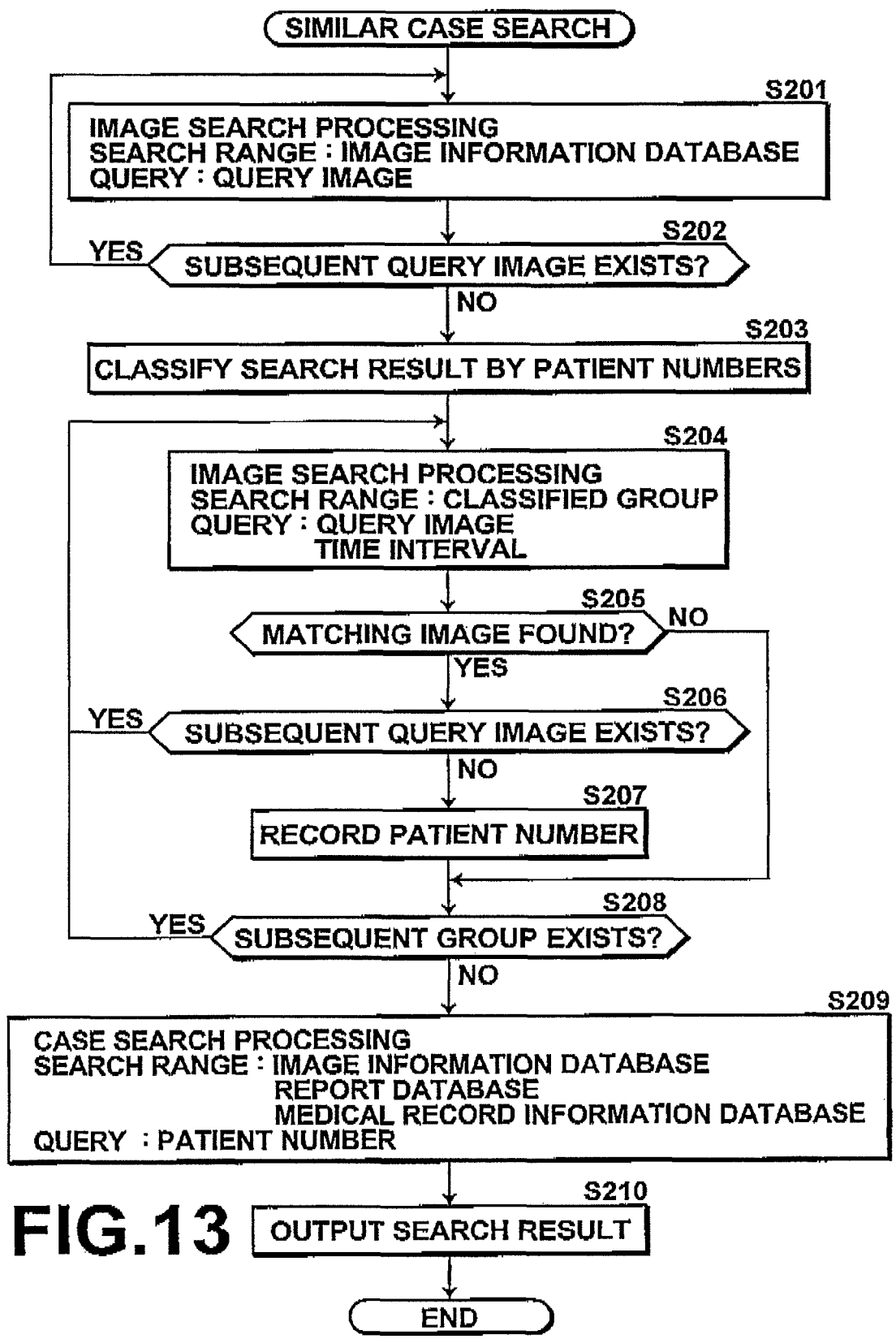
FIG. 13 is a flow chart showing similar case search processing based on the first similar case search procedures.

FIGS. 12 and 13 describe first search procedures. FIG. 12 is a schematic diagram of the processing while FIG. 13 is a flow chart thereof. In the first search procedures, a search range is set to be the image information sets in the image information database 5, and search is carried out for the images having the similar pictorial characteristics of ROI to the query image set first as a search query in the search condition information set 16. More accurately, the image information database 5 is searched for the image information sets including the image data representing such images, and the image information sets are extracted (S201). In the description below, "an image information set including image data representing an image" is simply referred to as "an image" upon necessity.

The image search processing at Step S201 is carried out until a subsequent one of the query images to be set as a search query does not exist (S202), regardless of whether the image information sets have been extracted as matches through the search. In other words, the image search processing at Step S201 is carried out for all the query images set in the search condition information set.

FIG. 12 shows an example in which four series of X-ray CT images of four patients obtained on different dates have been extracted in the search processing carried out for the first time by using as a search query the ROI image in the image obtained on Mar. 24 of 2006 (hereinafter referred to as the first query image) regarding a patient whose number is 4000 (hereinafter referred to as the patient 4000) while three plain X-ray images of three patients obtained on different dates and four plain X-ray images of four patients obtained on different dates have been extracted respectively in the search processing carried out for the second time by using as another search query the ROI image in the image obtained on Dec. 20 of 2005 (hereinafter referred to as the second query image) and in the search processing carried out for the third time by using as still another search query the ROI image in the image obtained on Apr. 10 of 2005 (hereinafter referred to as the third query image). In this embodiment, similarity/non-similarity in the pictorial characteristics is judged based on the characteristic quantities calculated from the query images, that is, from the ROI images. Therefore, even in the case where positions of the ROIs are different as shown in FIG. 12, the image information sets of the images having the similar pictorial characteristics to the ROI images are extracted through the search.

The similar case search means 23 then classifies a result of the search at Step S201, that is, the extracted images according to the patient number (S203). In the example shown in FIG. 12, image information sets obtained at three times have been extracted regarding the patient 2501. Therefore, the images are classified in one and the same group. In addition, image information sets obtained at two times have been extracted regarding the patient 3254, and the images are classified in one and the same group. Likewise, the images of other patients are classified in the same manner.

The similar case search means 23 then sets each of the groups defined at Step S203 as a search range, and searches for the images having ROIs of similar pictorial characteristics, by using the first query image as a search query (s204). In the case where the images having the similar pictorial characteristics have been extracted (S205), the similar case search means 23 judges whether the search condition information set has another one of the query images set therein as one of the search conditions (S206). The similar case search means 23 further refers to the value of the acquisition time interval between the query image and the previous query image in the search condition information set, and repeats the image search processing at Step S204 using the query image and the acquisition time interval as search queries. However, unlike the image search processing carried out for the first time at Step S204, the acquisition time interval is added as one of the search queries in the image search processing carried out for the second time or later. Therefore, images that are similar but have been obtained at different time intervals are not extracted.

The comparison of the acquisition time intervals is carried out in units of weeks, months or years, for example. In this embodiment, as has been described above, the acquisition time intervals have been set in half-month units in the search condition information set 16. Therefore, judgment is carried out in half-month units on whether the acquisition time intervals are the same. In the example shown in FIG. 12, the patient 2501 was examined on May 9 of 2002, Feb. 2 of 2002, and Jun. 7 of 2001, and image acquisition time intervals therebetween are 3 months and 8 months. Since the acquisition time intervals are the same as the query images, presence of the image information sets having the same time intervals is confirmed at Step S205.

In the case where the image information sets that match the two conditions comprising the query images and the acquisition time intervals have been extracted (S205), judgment is made again on whether the search condition information set includes another one of the query images as another one of the search conditions (S206). In the case where the search condition information set does not have another one of the query images as a search query, it means that the image information sets corresponding to all the query images set in the search condition information set have been extracted. Therefore, the similar case search means 23 refers to the patient number included in the accompanying information of the extracted image information sets, and records the patient number in a memory or the like of the DBMS 8 (S207). For example, three groups of images surrounded by a broken line are extracted in the processing from Steps S204 to S206 in the example in FIG. 12.

The similar case search means 23 judges whether another one of the groups exists (S208). In the case where a result of the judgment at Step S208 is affirmative, the processing from S204 to S207 is repeated. For example, the image search processing is carried out regarding the image information sets included in the group of the patient 3254 in the example in FIG. 12. For the group of the patient 3254, the time interval between the image corresponding to the first query image (the image obtained on Dec. 13 of 2001) and the image corresponding to the second query image (the image obtained on Feb. 14 of 2006) is 4 years and 2 months, which is longer. Therefore, in the image search processing at Step S204 using the 3-month time interval as one of the search queries, the image obtained on Feb. 14 of 2006 is not extracted. Consequently, judgment is made at Step S205 that no image information set exists as a match for the group of the patient 3254, and the patient number is not recorded at Step S207.

In the case where a subsequent one of the groups does not exist for the image search processing at Step S204 (S208), the similar case search means 23 sets the image information database 5, the image interpretation report database 6, and the medical record information database 7 as search ranges, and sets the patient number recoded in the memory at Step S207 as a search query for finding the case information sets 13 (S209). In detail, the similar case search means 23 firstly obtains the medical record information sets of the matching patients by searching the medical record information database 7, and obtains all the case information sets managed by the medical record information sets, by searching the image interpretation report database 6 and the image information database 5 according to the information on test number in the medical record information sets as has been described with reference to FIG. 5.

The similar case search means 23 outputs the case information sets obtained through the search at Step S209 as a result of similar case search. The case information sets are transferred to the radiologist workstation 3 and supplied to the case information display means 22.

Figure 15:
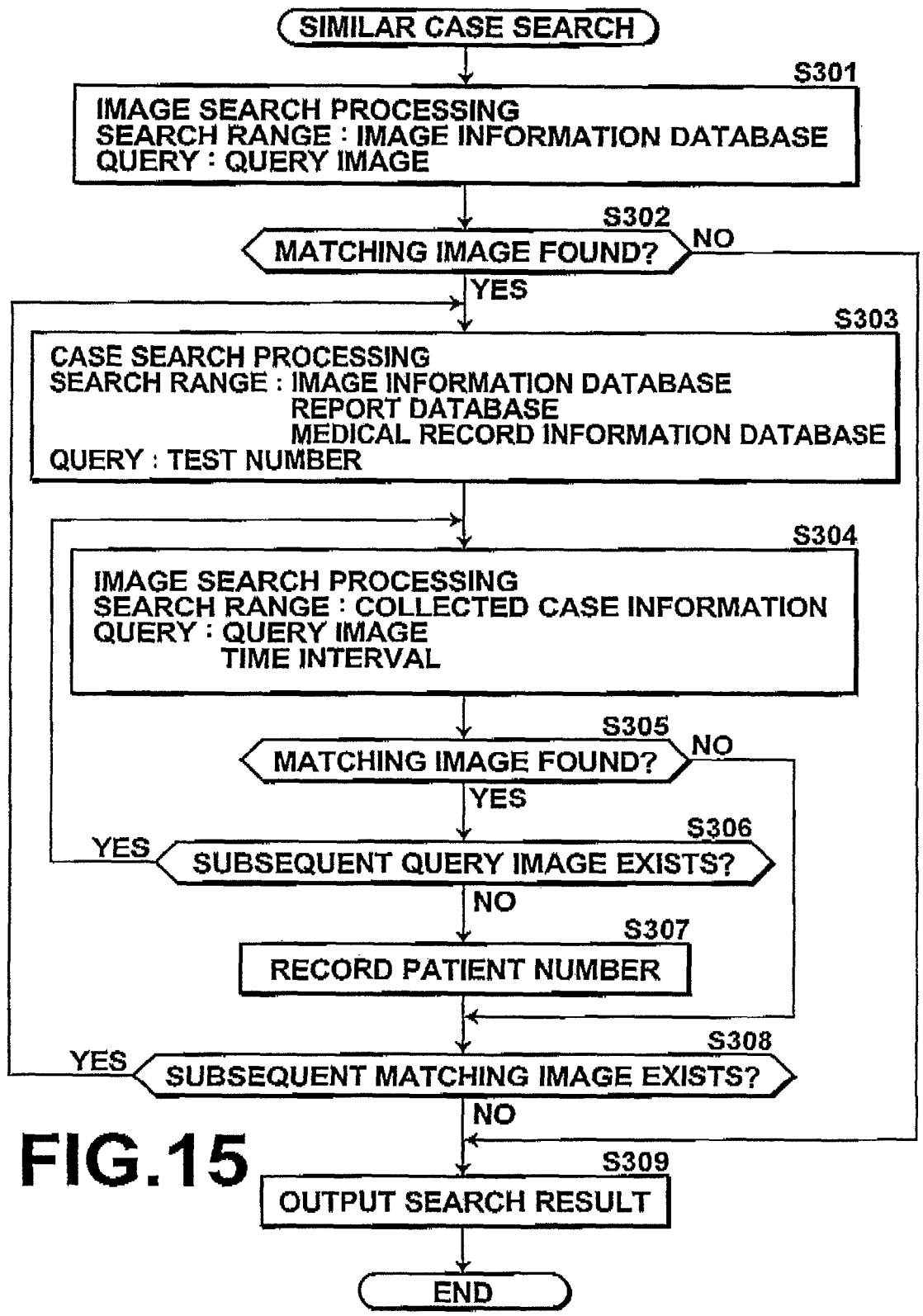
FIG. 15 is a flow chart showing similar case search processing based on the second similar case search procedures.

FIGS. 14 and 15 show second search procedures carried out by the similar case search means 23. FIG. 14 is a schematic diagram thereof while FIG. 15 is a flow chart thereof. In the second search procedures, the image information database 5 is firstly set as a search range and image search is carried out by using the first query image as a search query, which is the same as the first search procedures. However, in the first search procedures described above, the image information database 5 is searched until a subsequent one of the query images having been set as a search query does not exist regardless of whether the corresponding image information sets have been extracted. On the other hand, in the second search procedures, if no image information set (similar image) has been extracted as a match in the search carried out for the first time (S302), a search result representing nonexistence of corresponding image information set is outputted (S309) to end the procedures. In addition, even in the case where extraction of the corresponding image information sets have been affirmed at Step S302, search of the image information database 5 using the second and third query images as search queries is not carried out.

In the case where the image information sets have been extracted as matches at Steps S301 and S302 in the second search procedures, the similar case search means 23 obtains the test number included in the accompanying information of each of the image information sets, and carries out case information search by using the test number as a search query (S303). In detail, the image interpretation report corresponding to one of the matching images is obtained by searching the image interpretation report database 6 with the test number as a search query as shown by the relationships in FIG. 5, and the patient number recorded in the image interpretation report is referred to. By using the patient number as a search query, the medical record information database 7 is searched for the medical record information set of the patient. The image interpretation report database 6 is then searched again for the other image interpretation reports related to the medical record information set, by using the test number described in the medical record information set as a search query. Furthermore, the image information database 5 is searched for the image information sets of the interpretation target images in the image interpretation reports. In this manner, the similar case search means 23 obtains the case information sets to which the image information sets extracted at Step S301 belong.

Thereafter, the similar case search means 23 sets the collected and obtained case information sets as a search range at Step S303, and carries out image search by using the second query image and the time interval as search queries (S304). In the case where the corresponding image information sets have been extracted through the search (S305), judgment is carried out again on whether another one of the query images has been set as one of the search conditions (S306). If the query image to be used as the search query does not exist, it means that the image information sets corresponding to all the query images set in the search condition information set have been extracted. Therefore, the similar case search means 23 refers to the patient number included in the accompanying information of each of the image information sets having been extracted, and records the patient number in the memory or the like of the DBMS 8 (S307). For example, image information sets obtained at three times surrounded by a solid line in the example in FIG. 14 are extracted by the processing at Steps S304 to S306 in FIG. 15.

The similar case search means 23 judges whether another one of the image information sets extracted at Step S301 exists (S308). If a result of the judgment is affirmative, the processing from S304 to S307 is repeated. For example, image search is carried out regarding the image information sets included in the case information set of the patient 3254 in the example in FIG. 14. However, the acquisition time interval between the images (obtained on Dec. 13 of 2001) corresponding to the first query image and the image (obtained on Feb. 14 of 2006) corresponding to the second query image is not 3 months for the patient 3254. Therefore, the image information set generated on Feb. 14 of 2006 is not extracted. Consequently, no matching image information set has been judged to exist at Step S305, and the patient number is not recorded at Step S307.

In the case where the similar case search means 23 has judged that no other image information sets have been extracted at Step S301 (S308), the similar case search means 23 outputs the case information sets extracted through the case search processing as a result of the search (S309). The case information sets having been outputted are transferred to the radiologist workstation 3 and supplied to the case information display means 22.

How the case information display means 22 carries out screen control will be described next with examples of displayed screens. In this embodiment, the case information display means 22 divides a window whose display is controlled by an operating system into a plurality of frames, and respectively displays the case information sets supplied from the similar case search means 23 in the frames in a predetermined layout. As a method of displaying the case information sets, all the information supplied from the similar case search means 23 may be displayed. However, the case information display means 22 in this embodiment carries out display control so as to display the obtained case information sets in a stepwise manner by switching between a catalog display screen showing an outline result of the search and a detailed display screen showing the result in detail.

Figure 16:
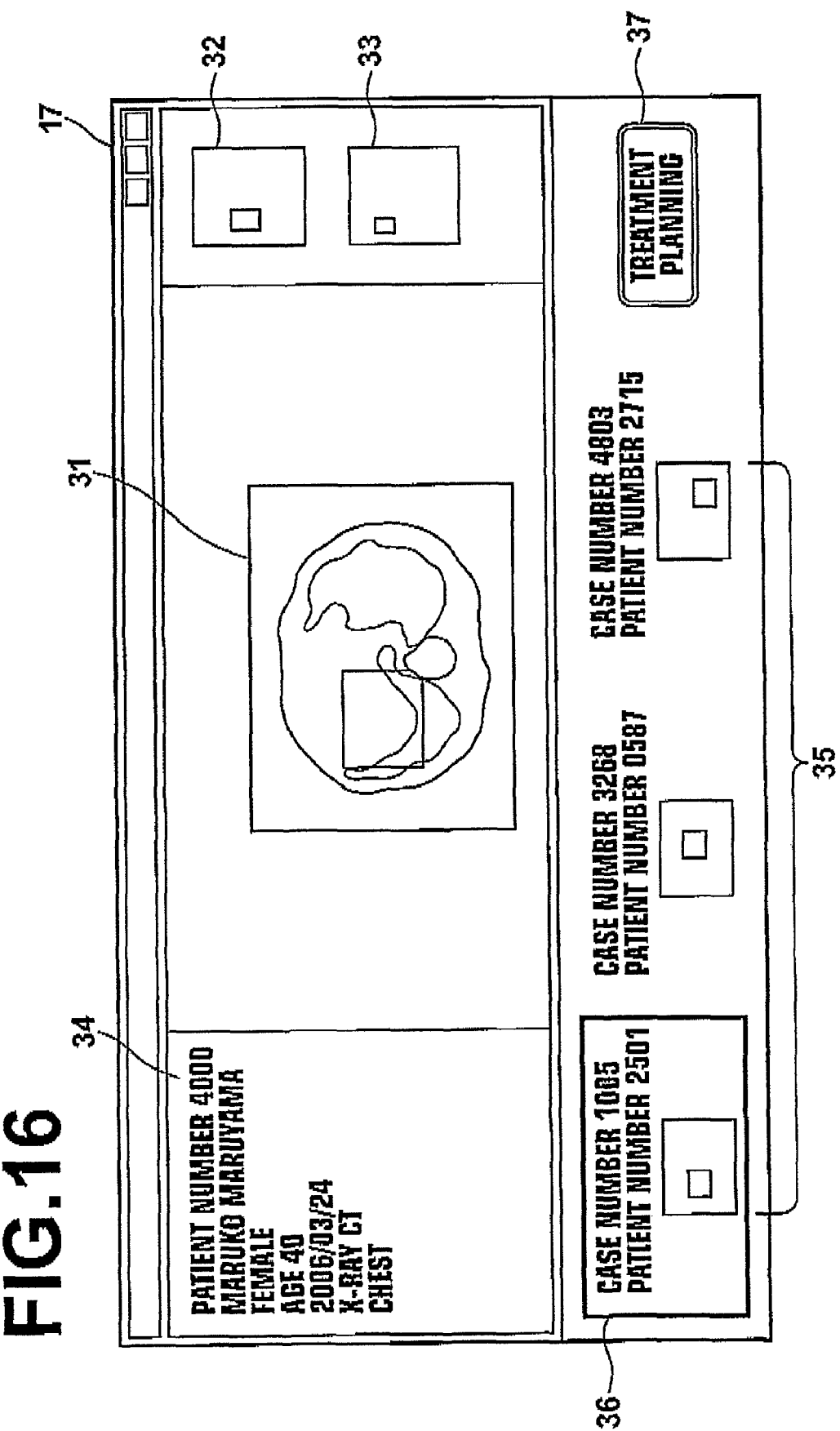
FIG. 16 shows an example of a search result catalog display screen.

FIG. 16 shows a layout example of a catalog display screen 17. In the example in FIG. 16, the window is divided into four frames comprising three frames in an upper portion thereof and one frame in a lower portion thereof. In the upper left frame, an information set 34 of the subject represented by the images used as the search queries is displayed while a medical image 31 obtained on the latest test date among the images used as the search queries is displayed in the frame in the middle of the upper portion. Past images 32 and 33 having older test dates among the images used as the search queries are also displayed in the upper right frame while a catalog 35 of similar cases extracted through the search is displayed in the lower frame. In this embodiment, an operation button 37 for calling up a treatment planning support screen is also located in the lower frame.

In this embodiment, the information displayed in each of the upper frames in the catalog display screen is the information having been set by the region of interest setting means 21. Therefore, the case information display means 22 obtains the information directly from the region of interest setting means 21, and displays the information at predetermined positions in the corresponding frames. The case information display means 22 controls display so as to cause the image information set comprising the case information set to be located and displayed at the predefined positions in the upper left and middle frames. For the upper right frame, the case information display means 22 carries out control so as to locate the past images at the predetermined positions in an initial state, and receives a selection operation from the past images being displayed. In the case where the case information display means 22 has detected the selection operation with use of a pointing device or the like, the case information display means 22 changes the positions and sizes of the respective images so as to display the selected past image in the upper middle frame in an enlarged size and to display the image having been displayed in the upper middle frame in the upper right frame in a reduced size.

For the lower frame, the case information display means 22 extracts the case numbers used as identifiers of the respective cases from the medical record information sets in the case information sets supplied from the similar case search means 23, and carries out control to list the case numbers in the frame. The list may comprise the case numbers alone displayed as selection items in a list box or a combo box. In this embodiment, the case numbers are displayed together with the patient numbers extracted from the medical record information sets as shown in FIG. 16, in addition to the reduced medical images recorded as the representative images in the corresponding medical record information sets or the corresponding image interpretation reports with frames representing the ROIs therein. At this time, in the case where the number of the cases is large, only a portion thereof is displayed, and the whole cases can be viewed by setting a horizontal scroll bar in the lower frame.

A selection operation is then received on any one of combinations of the case number, the patient number, and the reduced image, as surrounded by a frame 36 in FIG. 16. In the case where the selection operation with use of the pointing device or the like has been detected, the case information display means 22 opens a second window, and carries out display control of the detailed display screen in the second window.

For the lower frame, the case information display means 22 also receives a selection operation on the operation button 37. In the case where the selection operation has been detected, the case information display means 22 opens a third window and provides a treatment planning support function in the third window.

Figure 17:
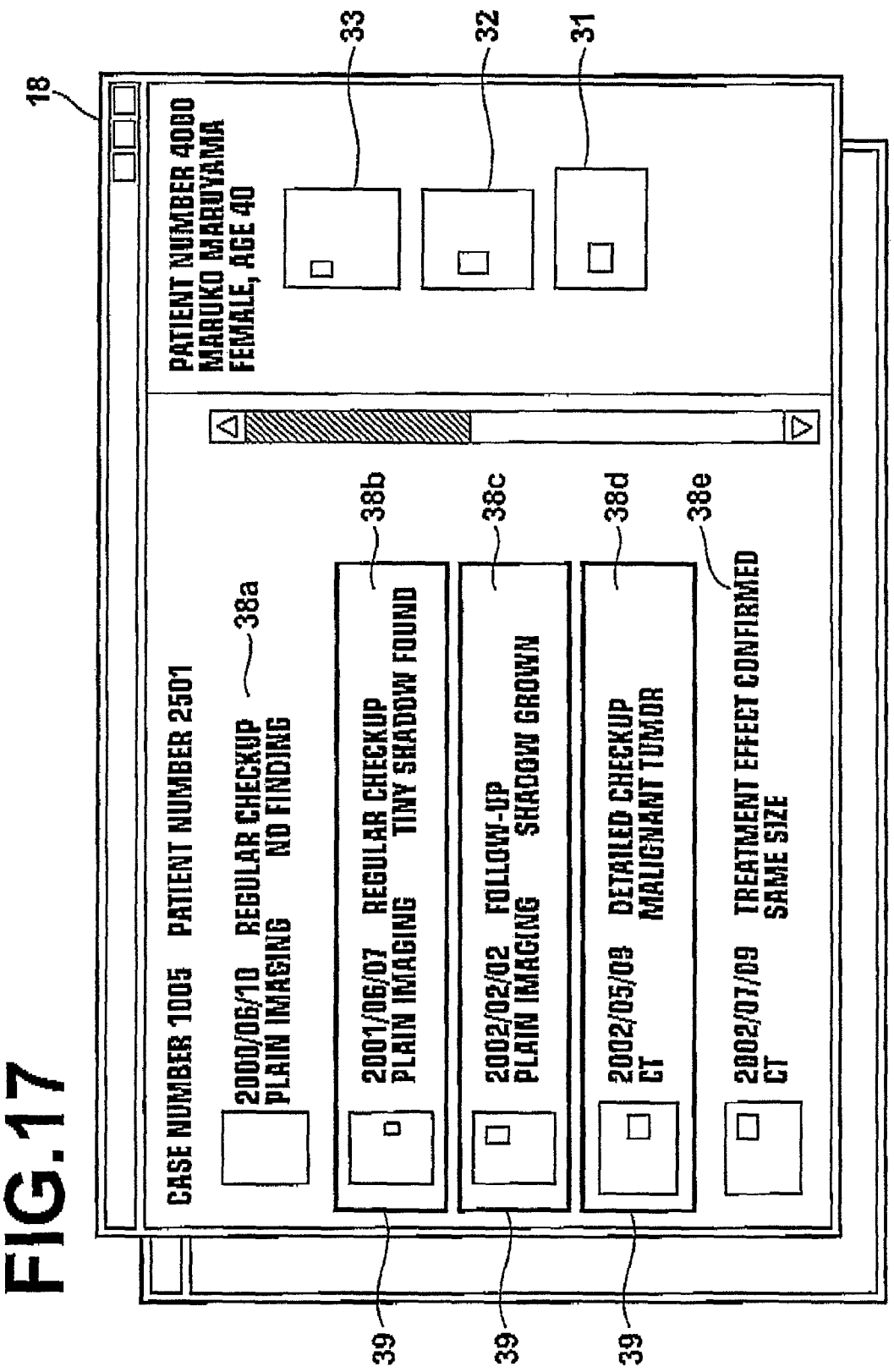
FIG. 17 is an example of a screen displaying a search result classified by cases.

An example of a layout of a detailed display screen 18 is shown in FIG. 17. In the example in FIG. 17, the window is divided into two frames at the right and the left. In the right frame, the information on the subject represented by the images as the search queries and the images 31, 32, and 33 used as the search queries are shown while the left frame has the detailed information on the case selected in the catalog display screen 17. FIG. 17 shows the example of the detailed display screen in the case where a case number 1005 surrounded by the frame 36 has been selected in the catalog display screen 17. In the layout in FIG. 17, all the test information recorded in the case information set of the case number 1005 is displayed in ascending chronological order from top to bottom, in addition to the images used as the search queries.

In the left frame, the case information display means 22 extracts all the image information sets and the image interpretation reports related thereto from the case information set identified by the selected case number, and carries out control so as to chronologically display at least a portion of items in the respective image information sets together with at least a portion of items of the image interpretation reports corresponding to the image information sets. In the example in FIG. 17, three items comprising the image data, the date of test, and the modality are shown for each of the image information sets while two items comprising the test purpose and the finding are shown for each of the image interpretation reports.

The order of test result information sets 38*a* to 38*e* each comprising the image data, the date of test, the modality, the test purpose, and the finding is determined so as to cause the test dates to be arranged in descending or ascending order according to the test date information. In the case where the number of the test result information sets is large, the case information display means 22 carries out control so as to display only a portion of the test result information sets and to enable all the test information included in the case information set to be viewed by setting a vertical scroll bar as shown in FIG. 17.

When the test result information sets are displayed in the chronological order, the case information display means 22 highlights the test result information sets including the images used by the similar case search means 23 to judge the degree of similarity. For example, FIG. 17 exemplifies the case where the test result information sets 38b, 38c, and 38d including the images corresponding to the query images are highlighted by being surrounded by frames 39.

Figure 18:
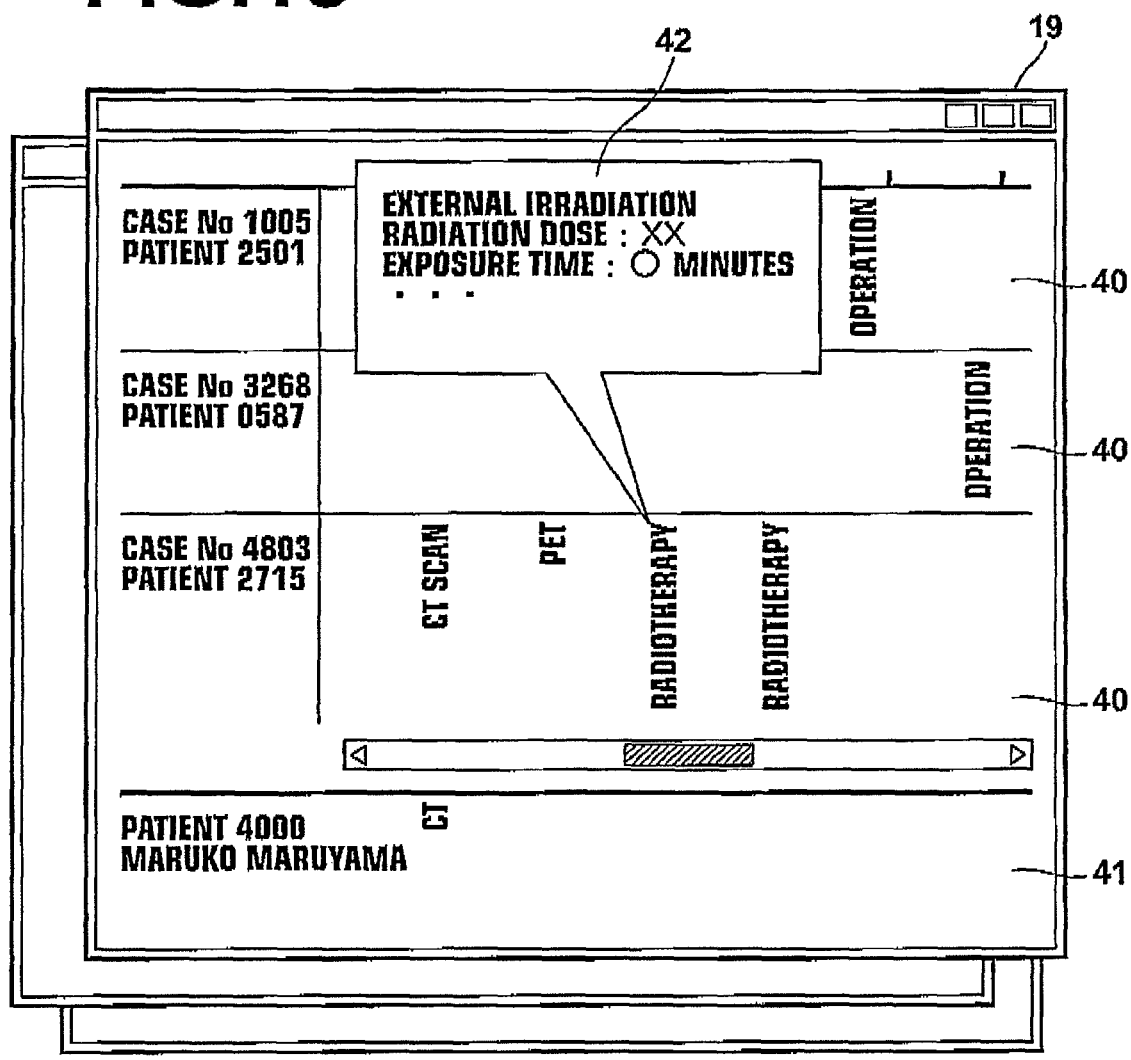
FIG. 18 shows an example of a treatment planning support screen.

FIG. 18 shows an example of a treatment planning support screen 19 called up when the operation button 37 is operated in the catalog display screen 17 in this embodiment. As shown in FIG. 18, the test history and the treatment history of the similar cases extracted through the search are displayed as charts in the screen. The case information display means 22 extracts the information of the test history and the treatment history from the medical record information sets included in each of the case information sets supplied from the similar case search means 23, and generates charts 40 in the screen by arranging the extracted information in the horizontal direction in chronological order. In this embodiment, the case information display means 22 enables comparison with the test history and the treatment history of the patient being diagnosed, by displaying a chart 41 of the history of the current patient at the bottom of the screen.

Furthermore, the case information display means 22 receives a specifying operation regarding test items and treatment items displayed in the charts 40. In the case where a selection operation by the pointing device has been received, the case information display means displays detailed items 42 regarding the specified test or treatment in a balloon as shown in FIG. 18. The detailed items 42 are displayed by extracting the image information set and the image interpretation report corresponding to the specified test from the case information set and by extracting the content of the items in the accompanying information of the image information set and in the image interpretation report.

FIG. 18 shows the state where only the information useful for treatment planning is displayed in the screen, out of the case information sets extracted through the search. However, in this embodiment, when one of the cases is selected from the charts 40 displayed in the screen, items of tests and treatments recommended in future are displayed at positions corresponding to the timings recommended for the tests and treatments in the chart 41. The items of recommended tests and treatments are displayed as characters in a different color from the past tests and treatments.

FIG. 19 is a flow chart schematically showing planning support processing that is carried out while the case information display means 22 controls the screen exemplified in FIG. 18. As shown in FIG. 19, when the case information display means 22 receives case selection by specifying one of the charts 40 (S401), the case information display means 22 compares the items of tests and treatments displayed in chart 41 of the current patient, that is, the items of tests and treatments carried out in the past to the items of tests and treatments recorded in the medical record information set and the image interpretation reports in the selected case information set, in order to relate the timings of the tests and the treatments (S402). The case information display means 22 then extracts the tests and treatments that were carried out in the selected case but have not been carried out on the current patient, and judges the recommended timings to carry out the tests and treatments (S403). For example, in the case where the current patient has just experienced his/her first CT scan and the selected case information set has a record of CT scans carried out regularly at 3-month intervals, it is judged that a subsequent one of the recommended tests is a CT scan and the recommended timing is 3 months later.

Thereafter, the case information display means 22 then refers to the medical record information set of the current patient, and obtains the information on age, previous diseases, allergies, use/non-use of pace maker, and the like (S404). The case information display means 22 judges whether execution of the tests and treatments extracted at Step S403 on the patient is innocuous (S405).

This judgment is carried out by storing in a memory or the like of each of the radiologist workstations 3 a table generated in advance for relating data that can be described in the medical record information sets and items of bans or restrictions corresponding to the data and by judging at Step S405 whether any one or more of the items on bans or restrictions apply to the current patient, with reference to the table. For example, the table predefines a ban of MR imaging test on a patient wearing a heart pace maker, bans on predetermined drugs for patients with predetermined allergies, an upper limit of allowed radiation dose on patients of predetermined age or younger, and the like.

In the case where the medical record information set is recorded with a symbol, a character, or the like representing wearing of heart pace maker while an MR imaging test is included in the tests extracted at Step S403, a warning is issued by using message display, a sound, a voice, or the like at Step S407.

In the case where the extracted tests pose no problems if a value such as the upper limit of radiation dose described above is adjusted, the content of the tests is optimized at Step S406. For example, assume that one of the case information sets extracted as a similar case has a record of execution of a test or treatment in which an adult patient is exposed to radiation. Meanwhile if the patient being diagnosed is an elderly or a child, a radiation dose and the number of exposures to radiation are set to be smaller. In the case where no optimization is especially necessary, the processing at Step S406 is practically omitted.

After the recommended tests and treatments and the timings of execution thereof have been determined through the processing described above, the case information display means 22 displays the recommended tests and treatments in the medical record 41 of the current patient, in the color different from the tests and treatments having been carried out (S408).

Instead of receiving specification of the chart 40 at Step S401, the case information set representing the case having been judged to have a highest degree of similarity at the time of similar case search may be selected automatically, and the processing from Step S402 is carried out on the case information set.

As has been described above, in the system in this embodiment, the images obtained chronologically are set as the search queries, and the cases of similar temporal change in the pictorial characteristics, that is, the cases of similar progression of the disease can be searched for. At this time, the pictorial characteristics are not affected by opinions or experience of a physician unlike a finding or the like inputted by a physician, and the cases of similar progression can be searched for based on the objective facts.

It is of course useful in terms of diagnosis support to provide information on a case showing similarity in characteristics to an image obtained at one time, as has been carried out by a conventional system. However, there area non-negligible number of cases in which the same shadows are observed at one time but eventually diagnosed to be different diseases after different progressions. Therefore, only the fact that pictorial characteristics are similar at one time may not be convincing to diagnose the same disease. However, in the case where similar shadows are observed at a plurality of times, diagnosis as the same disease is more convincing. In other words, the system in this embodiment enables provision of more useful information to physicians at the time of diagnosis than a conventional system, which contributes more to diagnosis by physicians.

The information on the cases of similar progression is useful not only for diagnosis but also for planning future tests. For example, during discussion of what kind of test should be carried out next, if information is provided as similar-progression case information regarding the case where cancer has been diagnosed after repetitive plain X-ray imaging and regarding the case where cancer has been diagnosed early after adopting a PET scan as a test carried out at the second time, a physician will consider execution of PET scan at an early stage. In addition, when the physician explains the necessity of the test to a patient and seeks an agreement from the patient, it becomes easier to obtain agreement by provision of such case information to the patient.

Likewise, the information on the cases of similar progression is useful for treatment planning. For example, although a method wherein a lesion is removed by an operation and a method of killing cancer cells by radiotherapy without an operation have been known as methods of cancer treatments, it may not be easy to make a decision on selection from the methods, depending on a size, a position, and age (stamina) of a patient. In such a case, if information on cases of similar progression is provided, a physician can cast aside doubts on his/her diagnosis by referring to a cured case of a patient who is close in age to the current patient.

Moreover, in the system in this embodiment, a plan of recommended future tests and treatments is provided by the planning support function exemplified in FIG. 19. Therefore, even a physician who does not have much experience can make a treatment plan by referring to treatments carried out by experienced physicians regarding cases of similar progression. In addition, if a case showing a remarkable effect of treatment exists, worries of a patient can be eased by showing such a case to the patient.

At this time, since the case information sets as a basis for generation of the recommended plan have been extracted by similarity/non-similarity judgment based on the pictorial characteristics rather than similarity/non-similarity judgment based on information inputted by physicians, planning of tests and treatments can be supported based on the information on the cases of truly similar progression.

In the system in this embodiment, in the case where the tests or treatments carried out in the cases of similar progression are not suitable for a patient being diagnosed, either warning is carried or a recommended plan adjusted to the patient is generated. Therefore, medical malpractice caused by judgment error can be prevented.

As has been described with reference to FIG. 1, the image information sets, the image interpretation reports, and the medical record information sets having been registered are related to each other and used as they are as the case information sets in this embodiment. However, an embodiment is also possible wherein image information sets, image interpretation reports, and a medical record information set having been registered in a period from first examination to complete recovery is registered as one case information set in a separate database at the time of treatment completion, for example. In this method, information on a case being treated cannot be referred to as a case information set, which is a demerit. However, fast search can be realized by narrowing a search range at the time of similar case search due to collective registration of image information sets, image interpretation reports, and medical record information sets in the one location, and by causing a format of the case information set to be appropriate for the search.

The formats of the information to be registered with the databases and the search procedures by the similar case search means can also be determined appropriately in consideration of a search speed or restrictions on the existing databases and systems. In addition, the user interface of the region of interest setting means 21 and the layout of the screens whose display is controlled by the case information display means 22 can be determined appropriately. In other words, the examples in the above embodiment are mere examples, and do not limit the scope of the present invention.

The invention claimed is:

1. A diagnosis support system that supports diagnosis based on interpretation of a given medical image by searching case information sets registered with a database for case information sets including case images of similar pictorial characteristics to the given medical image and by displaying the case information sets including the case images, the system comprising:

region of interest setting means for setting a region of interest in each of medical images obtained in chronological order, by displaying the medical images on a monitor screen and by receiving a region specifying operation on at least one of the medical images;

similar case search means for extracting through search of the database a case information set including case images each having a region representing pictorial characteristics that are similar to pictorial characteristics of a corresponding one of the regions of interest having been set by the region of interest setting means;

case information display means for displaying all the case images belonging to the case information set extracted by the similar case search means on the monitor screen in chronological order; and further comprising corresponding region estimating means for estimating in a second one of the medical images a region representing a target that is the same as a target represented by a region specified in a first one of the medical images according to coordinate information identifying the region specified in the first medical image, wherein the region of interest setting means receives specification of the region of interest by the region specifying operation only in one of the medical images and sets the region of interest in each of the medical images by causing the corresponding region estimating means to estimate the region of interest in each of the remaining images by supplying the coordinate information identifying the specified region thereto.

2. The diagnosis support system according to claim 1, wherein the similar case search means carries out processing for searching for case images each having a region representing pictorial characteristics that are similar to the pictorial characteristics of a corresponding one of the regions of interest having been set by the region of interest setting means;

processing for identifying a group of case images of one and the same patient each having the region representing the pictorial characteristics that are similar to the pictorial characteristics of the corresponding region of interest having been set by the region of interest setting means among the case images having been detected through the search for the case images; and processing for supplying a case information set including the case images belonging to the identified group to the case information display means as the case information set having been extracted through the search of the database.

3. The diagnosis support system according to claim 1, wherein the similar case search means carries out processing for searching for case images each having a region representing pictorial characteristics that are similar to pictorial characteristics of the region of interest in one of the medical images having been set by the region of interest setting means;

processing for further searching for case images respectively having regions representing pictorial characteristics that are similar to pictorial characteristics of the regions of interest in the medical images excluding the one medical image by setting case information sets including the case images extracted through the search for the case images as a search range; and processing for supplying a case information set from which the case images respectively having the regions representing the pictorial characteristics that are similar to the pictorial characteristics of the regions of interest in the corresponding medical images other than the one medical image have been extracted to the case information display means as the case information set having been extracted through the search of the database.

4. The diagnosis support system according to claim 1, further comprising:

time interval setting means for setting an acquisition time interval between the medical images, wherein the similar case search means searches the database for a case information set that includes case images obtained at a time interval equal to the time interval having been set by the time interval setting means and respectively have the regions representing the pictorial characteristics that are similar to the pictorial characteristics of the regions of interest in the corresponding medical images having been set by the region of interest setting means.

5. The diagnosis support system according to claim 1, wherein the case information display means collectively displays only identifiers of the extracted case information sets, receives an operation of selection from the identifiers, and displays all the case images belonging to the case information set represented by the identifier selected by the operation, in chronological order of acquisition of the case images.

6. The diagnosis support system according to claim 1, wherein the case information display means displays the case images respectively having the regions representing the pictorial characteristics that are similar to the pictorial characteristics of the regions of interest, distinctly from the other case images included in the case information set to which the case images belong.

* * * * *